(12) United States Patent
Hashimshony et al.

(10) Patent No.: US 11,179,053 B2
(45) Date of Patent: Nov. 23, 2021

(54) GRAPHICAL USER INTERFACES (GUI), METHODS AND APPARATUS FOR DATA PRESENTATION

(71) Applicant: DILON MEDICAL TECHNOLOGIES LTD., Caesarea (IL)

(72) Inventors: Dan Hashimshony, Givat Ada (IL); Orit Yarden, Givat Shmuel (IL); Gal Aharonowitz, Moshav Gan Haim (IL); Gil Cohen, Jerusalem (IL)

(73) Assignee: Dilon Medical Technologies LTD., Caesarea (IL)

( * ) Notice: Subject to any disclaimer, the term of this patent is extended or adjusted under 35 U.S.C. 154(b) by 283 days.

(21) Appl. No.: 15/665,829

(22) Filed: Aug. 1, 2017

(65) Prior Publication Data
US 2018/0055404 A1   Mar. 1, 2018

Related U.S. Application Data

(63) Continuation of application No. 12/483,738, filed on Jun. 12, 2009, now Pat. No. 9,750,425, which is a
(Continued)

(51) Int. Cl.
*A61B 5/05* (2021.01)
*A61B 8/08* (2006.01)
(Continued)

(52) U.S. Cl.
CPC ............... *A61B 5/05* (2013.01); *A61B 5/064* (2013.01); *A61B 8/0858* (2013.01); *A61B 34/25* (2016.02);
(Continued)

(58) Field of Classification Search
CPC ........... A61B 5/05; A61B 5/064; A61B 5/065; A61B 5/0084; A61B 5/015; A61B 5/053;
(Continued)

(56) References Cited

U.S. PATENT DOCUMENTS 3,830,224 A   8/1974   Vanzetti et al.
4,291,708 A   9/1981   Frei et al.
(Continued)

FOREIGN PATENT DOCUMENTS

AU   688352 B2   3/1998
CN   1145213 A   3/1997
(Continued)

OTHER PUBLICATIONS

Akerman, M. E. et al., "Nanocrystal Targeting in vivo," PNAS, Oct. 1, 2002, vol. 99 No. 20, pp. 12617-12621.
(Continued)

*Primary Examiner* — Matthew Kremer
*Assistant Examiner* — Avery M Foley
(74) *Attorney, Agent, or Firm* — Browdy and Neimark, PLLC

(57) ABSTRACT

A graphical user interface (GUI) including: (a) a group definition module adapted to accept a user input defining groups; (b) a data receiver operable to receive a plurality of individual measurement input datum indicative of status of a substrate; (c) a grouping module configured to assign each of said individual measurement input datum to one of said groups to produce grouped data; and (d) an output module adapted to output the grouped data.

17 Claims, 22 Drawing Sheets

Related U.S. Application Data continuation-in-part of application No. PCT/IL2007/001539, filed on Dec. 12, 2007, and a continuation-in-part of application No. 11/745,334, filed on May 7, 2007, now Pat. No. 7,904,145, which is a continuation-in-part of application No. 11/743,028, filed on May 1, 2007, now abandoned, which is a continuation-in-part of application No. 10/558,831, filed as application No. PCT/IL2005/000330 on Mar. 23, 2005, now Pat. No. 7,720,532, said application No. 12/483,738 is a continuation-in-part of application No. 11/743,028, filed on May 1, 2007, now abandoned.

(60) Provisional application No. 60/914,822, filed on Apr. 30, 2007, provisional application No. 60/874,280, filed on Dec. 12, 2006, provisional application No. 60/555,901, filed on Mar. 23, 2004.

(51) Int. Cl.
| | | |
|---|---|---|
| *G06F 3/0481* | (2013.01) | |
| *A61B 5/06* | (2006.01) | |
| *A61B 34/00* | (2016.01) | |
| *G16H 40/63* | (2018.01) | |
| *G16H 50/50* | (2018.01) | |
| *G16H 20/40* | (2018.01) | |
| *G16H 30/20* | (2018.01) | |
| *G06F 19/00* | (2018.01) | |
| *A61B 5/00* | (2006.01) | |
| *A61B 5/01* | (2006.01) | |
| *A61B 5/053* | (2021.01) | |
| *A61B 8/12* | (2006.01) | |
| *A61B 34/20* | (2016.01) | |
| *A61B 34/30* | (2016.01) | |
| *A61B 90/00* | (2016.01) | |

(52) U.S. Cl.
CPC ............ *G06F 3/0481* (2013.01); *G06F 19/00* (2013.01); *G16H 20/40* (2018.01); *G16H 30/20* (2018.01); *G16H 40/63* (2018.01); *G16H 50/50* (2018.01); *A61B 5/0084* (2013.01); *A61B 5/015* (2013.01); *A61B 5/053* (2013.01); *A61B 5/06* (2013.01); *A61B 8/12* (2013.01); *A61B 34/20* (2016.02); *A61B 34/30* (2016.02); *A61B 2090/061* (2016.02); *A61B 2562/0233* (2013.01); *A61B 2562/046* (2013.01)

(58) Field of Classification Search
CPC ........... A61B 5/06; A61B 34/25; A61B 34/20; A61B 34/30; A61B 2034/252; A61B 2034/254; A61B 2034/2074; A61B 8/0858; A61B 8/0841; A61B 8/08; A61B 8/12; A61B 2090/061; A61B 2562/0233; A61B 2562/046; G16H 50/50; G16H 40/60; G16H 20/40; G16H 30/20; G06F 3/0481; G06F 3/04812; G06F 19/00; G06F 19/321; G06F 19/3481
See application file for complete search history.

(56) References Cited

U.S. PATENT DOCUMENTS

| | | |
|---|---|---|
| 4,344,440 A | 8/1982 | Aaby et al. |
| 4,458,694 A | 7/1984 | Sollish et al. |
| 4,537,203 A | 8/1985 | Machida |
| 4,539,640 A | 9/1985 | Fry et al. |
| RE32,000 E | 10/1985 | Sagi |
| 4,617,939 A | 10/1986 | Brown et al. |
| 4,625,171 A | 11/1986 | Sekihara et al. |
| 4,682,594 A | 7/1987 | Mok |
| 4,689,567 A | 8/1987 | Maudsley |
| 4,751,464 A | 6/1988 | Bridges |
| 4,768,513 A | 9/1988 | Suzuki |
| 4,785,806 A | 11/1988 | Deckelbaum |
| 5,115,137 A | 5/1992 | Andersson-Engels et al. |
| 5,143,079 A | 9/1992 | Frei et al. |
| 5,227,730 A | 7/1993 | King et al. |
| 5,383,454 A | 1/1995 | Bucholz |
| 5,442,290 A | 8/1995 | Crooks |
| 5,482,041 A | 1/1996 | Wilk et al. |
| 5,546,951 A | 8/1996 | Ben-Haim |
| 5,558,092 A | 9/1996 | Unger et al. |
| 5,572,132 A | 11/1996 | Pulyer et al. |
| 5,615,132 A | 3/1997 | Horton et al. |
| 5,630,426 A | 5/1997 | Eggers et al. |
| 5,678,565 A | 10/1997 | Sarvazyan |
| 5,699,804 A | 12/1997 | Rattner |
| 5,704,355 A | 1/1998 | Bridges |
| 5,727,569 A | 3/1998 | Benetti et al. |
| 5,735,278 A | 4/1998 | Hoult et al. |
| 5,744,971 A | 4/1998 | Chan et al. |
| 5,758,646 A | 6/1998 | Van Der Meulen et al. |
| 5,800,350 A | 9/1998 | Coppleson et al. |
| 5,807,257 A | 9/1998 | Bridges |
| 5,810,742 A | 9/1998 | Pearlman |
| 5,821,410 A | 10/1998 | Xiang et al. |
| 5,829,437 A | 11/1998 | Bridges |
| 5,884,239 A | 3/1999 | Romanik, Jr. |
| 5,900,618 A | 5/1999 | Anlage et al. |
| 5,927,284 A | 7/1999 | Borst et al. |
| 6,010,455 A | 1/2000 | Barnett et al. |
| 6,026,323 A | 2/2000 | Skladnev et al. |
| 6,030,344 A | 2/2000 | Guracar ............ A61B 6/08 |
| | | 600/447 |
| 6,055,452 A | 4/2000 | Pearlman |
| 6,057,924 A | 5/2000 | Ross ............ G01B 11/06 |
| | | 356/503 |
| 6,061,589 A | 5/2000 | Bridges et al. |
| 6,064,081 A | 5/2000 | Robinson et al. |
| 6,071,239 A | 6/2000 | Cribbs et al. |
| 6,086,534 A | 7/2000 | Kesten |
| 6,090,041 A | 7/2000 | Clark et al. |
| 6,091,981 A | 7/2000 | Cundari ............ A61B 5/0053 |
| | | 600/407 |
| 6,109,270 A | 8/2000 | Mah et al. |
| 6,135,968 A | 10/2000 | Brounstein |
| 6,167,297 A * | 12/2000 | Benaron ............ A61B 5/0071 |
| | | 600/431 |
| 6,173,604 B1 | 1/2001 | Xiang et al. |
| 6,203,778 B1 | 3/2001 | Brasch ............ A61K 49/0428 |
| | | 424/9.411 |
| 6,226,542 B1 | 5/2001 | Reisfeld |
| 6,233,479 B1 | 5/2001 | Haddad et al. |
| 6,258,576 B1 | 7/2001 | Richards-Kortum et al. |
| 6,280,704 B1 | 8/2001 | Schutt et al. |
| 6,287,302 B1 | 9/2001 | Berube |
| 6,301,496 B1 | 10/2001 | Reisfeld |
| 6,308,097 B1 | 10/2001 | Pearlman |
| 6,315,981 B1 | 11/2001 | Unger |
| 6,321,106 B1 | 11/2001 | Lemelson |
| 6,331,166 B1 | 12/2001 | Burbank et al. |
| 6,363,940 B1 * | 4/2002 | Krag ............ A61B 90/39 |
| | | 128/899 |
| 6,370,426 B1 | 4/2002 | Campbell et al. |
| 6,375,634 B1 | 4/2002 | Carroll |
| 6,377,841 B1 | 4/2002 | Lin et al. |
| 6,397,095 B1 | 5/2002 | Eyuboglu et al. |
| 6,405,733 B1 | 6/2002 | Fogarty et al. |
| 6,409,684 B1 | 6/2002 | Wilk ............ A61B 7/00 |
| | | 600/484 |
| 6,500,112 B1 | 12/2002 | Khouri |
| 6,530,944 B2 | 3/2003 | West et al. |
| 6,546,787 B1 | 4/2003 | Schiller et al. |
| 6,552,337 B1 | 4/2003 | Cho ............ B82Y 35/00 |
| | | 257/E21.53 |

(56) References Cited

U.S. PATENT DOCUMENTS

| | | | |
|---|---|---|---|
| 6,564,806 B1 | 5/2003 | Fogarty et al. | |
| 6,569,160 B1 | 5/2003 | Goldin | |
| 6,597,185 B1 | 7/2003 | Talanov et al. | |
| 6,631,292 B1 | 10/2003 | Liedtke | A61B 5/053 600/547 |
| 6,671,540 B1 | 12/2003 | Hochman | |
| 6,677,755 B2 | 1/2004 | Belt et al. | |
| 6,690,963 B2 | 2/2004 | Ben-Haim | |
| 6,695,782 B2 | 2/2004 | Ranucci et al. | |
| 6,699,206 B2 | 3/2004 | Burbank et al. | |
| 6,722,371 B1 | 4/2004 | Fogarty et al. | |
| 6,728,565 B2 | 4/2004 | Wendlandt | |
| 6,731,966 B1 | 5/2004 | Spigelman et al. | |
| 6,741,077 B2 | 5/2004 | Yokoyama et al. | |
| 6,747,454 B2 | 6/2004 | Belt | |
| 6,752,154 B2 | 6/2004 | Fogarty et al. | |
| 6,766,185 B2 | 7/2004 | Scott | |
| 6,813,515 B2 | 11/2004 | Hashimshony | |
| 6,833,814 B2 | 12/2004 | Gilboa et al. | |
| 6,840,948 B2 | 1/2005 | Albrecht et al. | |
| 6,892,091 B1 | 5/2005 | Ben-Haim | |
| 6,909,084 B2 | 6/2005 | Tachi et al. | |
| 6,962,587 B2 | 11/2005 | Johnson et al. | |
| 6,968,511 B1 | 11/2005 | Robertson et al. | |
| 7,082,325 B2 | 7/2006 | Hashimshony et al. | |
| 7,184,824 B2 | 2/2007 | Hashimshony | |
| 7,505,811 B2 | 3/2009 | Hashimshony | |
| 7,507,235 B2* | 3/2009 | Keogh | A61B 17/0206 128/898 |
| 7,515,769 B2 | 4/2009 | Akao et al. | 382/282 |
| 7,635,087 B1 | 12/2009 | Chung | G06K 7/14 235/386 |
| 8,160,690 B2 | 4/2012 | Wilfley et al. | 600/547 |
| 2001/0036304 A1 | 11/2001 | Yang et al. | |
| 2001/0051774 A1 | 12/2001 | Littrup et al. | |
| 2002/0055754 A1 | 5/2002 | Ranucci et al. | |
| 2002/0059938 A1 | 5/2002 | Fogarty et al. | |
| 2002/0068880 A1 | 6/2002 | Burbank et al. | |
| 2002/0075330 A1 | 6/2002 | Rosenzweig et al. | |
| 2002/0120265 A1 | 8/2002 | Fowler | |
| 2003/0045798 A1 | 3/2003 | Hular et al. | |
| 2003/0062897 A1 | 4/2003 | Belt et al. | |
| 2003/0081216 A1 | 5/2003 | Ebert | H01L 21/67259 356/445 |
| 2003/0117140 A1 | 6/2003 | Belt et al. | |
| 2003/0138378 A1 | 7/2003 | Hashimshony | |
| 2003/0171664 A1 | 9/2003 | Wendlandt | |
| 2003/0187349 A1 | 10/2003 | Kaneko et al. | |
| 2003/0187366 A1 | 10/2003 | Hashimshony | |
| 2003/0199753 A1 | 10/2003 | Hibner et al. | |
| 2003/0216648 A1 | 11/2003 | Lizzi et al. | |
| 2003/0229343 A1 | 12/2003 | Albrecht et al. | |
| 2004/0009459 A1* | 1/2004 | Anderson | G06T 19/00 434/262 |
| 2004/0024311 A1* | 2/2004 | Quaid, III | A61B 17/3403 600/428 |
| 2004/0054248 A1 | 3/2004 | Kimchy et al. | |
| 2004/0085443 A1 | 5/2004 | Kallioniemi | G01N 1/36 348/135 |
| 2004/0168692 A1 | 9/2004 | Fogarty et al. | |
| 2004/0176683 A1* | 9/2004 | Whitin | A61B 5/064 600/424 |
| 2004/0252809 A1 | 12/2004 | Kotian | A61B 5/4441 378/196 |
| 2004/0254454 A1* | 12/2004 | Kockro | A61B 90/36 600/424 |
| 2004/0258295 A1 | 12/2004 | Tiemeyer | G01N 21/9501 382/145 |
| 2005/0010131 A1 | 1/2005 | Burbank et al. | |
| 2005/0020918 A1* | 1/2005 | Wilk | A61B 5/6804 600/439 |
| 2005/0021019 A1 | 1/2005 | Hashimshony et al. | |
| 2005/0107717 A1 | 5/2005 | Yamamoto et al. | |
| 2005/0191390 A1 | 9/2005 | Krochta | A23G 1/305 426/302 |
| 2005/0267365 A1 | 12/2005 | Sokulin | A61B 5/1075 600/437 |
| 2005/0283078 A1 | 12/2005 | Steen | A61B 8/06 600/447 |
| 2006/0079746 A1 | 4/2006 | Perret | A61B 5/02007 600/407 |
| 2006/0088217 A1 | 4/2006 | Akoa | G06K 9/0014 382/191 |
| 2006/0107218 A1 | 5/2006 | Clark et al. | |
| 2006/0142971 A1 | 6/2006 | Reich | G01C 17/00 702/150 |
| 2006/0193538 A1 | 8/2006 | Vronay et al. | |
| 2006/0253107 A1 | 11/2006 | Hashimshony et al. | |
| 2006/0264738 A1 | 11/2006 | Hashimshony et al. | |
| 2007/0032739 A1 | 2/2007 | Hashimshony et al. | |
| 2007/0032747 A1 | 2/2007 | Hashimshony et al. | |
| 2007/0038084 A1 | 2/2007 | Burla | A61B 5/02007 600/437 |
| 2007/0106282 A1* | 5/2007 | Lavallee | A61B 34/20 606/1 |
| 2007/0179397 A1 | 8/2007 | Hashimshony et al. | |
| 2007/0255169 A1 | 11/2007 | Hashimshony et al. | |
| 2008/0021343 A1 | 1/2008 | Hashimshony et al. | |
| 2008/0216334 A1 | 9/2008 | Pak | A61B 5/448 33/512 |
| 2008/0221484 A1 | 9/2008 | Sarvazyan et al. | |
| 2009/0005682 A1 | 1/2009 | Fan | A61B 6/485 600/443 |
| 2009/0028461 A1 | 1/2009 | Wieringa | A61B 5/0059 382/284 |
| 2009/0192393 A1 | 7/2009 | Hayam et al. | |
| 2009/0262109 A1 | 10/2009 | Markowitz et al. | |
| 2009/0297001 A1 | 12/2009 | Markowitz et al. | |
| 2010/0004550 A1 | 1/2010 | Ishay et al. | |
| 2011/0021903 A1 | 1/2011 | Strommer et al. | |

FOREIGN PATENT DOCUMENTS

| | | |
|---|---|---|
| DE | 3637549 A1 | 5/1988 |
| EP | 0419235 A1 | 3/1991 |
| EP | 0 650 694 A1 | 10/1994 |
| GB | 2324450 A | 10/1998 |
| JP | A-2005-251075 | 9/2005 |
| WO | 9712553 A1 | 4/1997 |
| WO | WO 97/20193 A1 | 6/1997 |
| WO | 200208578 A1 | 2/2001 |
| WO | WO 2001/08578 | 2/2001 |
| WO | 0143630 A2 | 6/2001 |
| WO | 01/54067 A2 | 7/2001 |
| WO | 0165240 A1 | 9/2001 |
| WO | 01/90949 A1 | 11/2001 |
| WO | 03060462 A2 | 7/2003 |
| WO | 2005009200 A2 | 2/2005 |
| WO | 2005089065 A2 | 9/2005 |
| WO | 2006072947 A2 | 7/2006 |
| WO | 2006092797 A2 | 9/2006 |
| WO | 2006103665 A2 | 10/2006 |
| WO | 2007015255 A2 | 2/2007 |
| WO | 2009134605 A2 | 11/2009 |

OTHER PUBLICATIONS

Ascension Products—miniBIRD 500 & 800, http://www.ascension-tech.com/products/minibird.php, downloaded Nov. 26, 2007.

Beard, M. C. et al., "Size-Dependent Photoconductivity in CdSe Nanoparticles as Measured by Time-Resolved Terahertz Spectroscopy," Nano Letters, 2 (9), 983-987, Aug. 14, 2002—Abstract only.

Biosensors & Bioelectronics, vol. 20. Issue 1, pp. 1-142 (Jul. 30, 2004)—table of contents pages only.

Biosensors & Bioelectronics, vol. 20. Issue 5, pp. 917-1028 (Nov. 15, 2004) — table of contents pages only.

Biosensors & Bioelectronics, vol. 20. Issue 6, pp. 1029-1295 (Dec. 15, 2004)—table of contents pages only.

Biosensors & Bioelectronics, vol. 20. Issue 8, pp. 1459-1695 (Feb. 15, 2005)—table of contents pages only.

(56) References Cited

OTHER PUBLICATIONS

Biosensors & Bioelectronics, vol. 20. Issue 12, pp. 2387-2593 (Jun. 15, 2005)—table of contents pages only.
Cole, K. S., "Membranes, Ions and Impulses, A chapter of classical biophysics," Berkeley and Los Angeles: University of California Press, 1968—cover and table of contents pages only.
Dexter, L. I, et al., "Thermography in differential diagnosis of lymphostasis in the lower limbs," Vestn Khir Im I I Grek. Jun. 1976; 116(6):60-4—Abstract only.
Gopel, W., et al., Eds., "Sensors: A comprehensive survey, vol. 2: Chemical and biochemical sensors, Part I," Weinheim: VCH, 1991—table of contents pages only.
Gopel, W., et al., Eds., "Sensors: A comprehensive survey, vol. 3: Chemical and biochemical sensors, Part II," Weinheim: VCH, 1992—table of contents pages only.
Gopel, W., et al., Eds., "Sensors: A comprehensive survey, vol. 7: Mechanical sensors," Weinheim: VCH, 1994—table of contents pages only.
Grimnes, S et al., "Bioimpedance and Bioelectricity Basics," San Diego: Academic Press, 2000—cover and table of contents pages only.
Harzbecker, K, et al., "Thermographic thorax diagnostics," Z Gesamte Inn Med. Feb. 1, 1978:33(3):78-80—Abstract only.
Kinouch, Y et al., "Fast In-Vivo Measurement of Local Tissue Impedance Using Needle Electrodes," Med. Biol Eng. Comput. 35(9):486 492, 1997—Abstract only.
Pethig, R., "Dielectric and Electronic Properties of Biological Materials," Chichester: John Wiley & Sons, 1979—cover and table of contents pages only.
Proakis, J. G. et al., "Digital Signal Processing," Upper Saddle River: Prentice-Hall Inc., 1996, chapter 4—cover and table of contents pages only.
Rogers, K. R. et al., Eds., "Affinity Biosensors: Techniques and Protocols," Totowa: Hummana Press, 1998—table of contents pages only.
Schwan, H. P., "Mechanisms Responsible for Electrical Properties of Tissue and Cell Suspensions," Med. Prog. Tech. 19:163-165, 1993.
Section on Biomedical Stochastic Physics (SBSP), "Subsurface Spectroscopy," http://www.sbsp-limb.nichd.nih.gov/html/spectroscopy.html, downloaded Nov. 26, 2007.
Sensors & Actuators B: Chemical, vol. 102, Issue 1, pp. 1-177 (Sep. 2004)—table of contents pages only.
Sensors & Actuators B: Chemical, vol. 103, Issues 1-2, pp. 1-473 (Sep. 29, 2004)—table of contents pages only.
Sensors & Actuators B: Chemical, vol. 106, Issue 1, pp. 1-488 (Apr. 29, 2005)—table of contents pages only.
Smith, D. G. et al. "In Vivo Measurement of Tumor Conductiveness With the Magnetic Bioimpedance Method," IEEE Transactions on Biomedical Engineering, 47(10): 1403-1405, 2000.
Surowiex, A. J. et al, "Dielectric Properties of Breast Carcinoma and the Surrounding Tissues," IEEE Trans. Biomed. Eng. 35(4):257-262, 1988.
U.S. Appl. No. 60/641,081 to Dan Hashimshony, filed Jan. 4, 2005, entitled "Device and Method for Tissue Characterization in a Body Lumen, by an Endoscopic Electromagnetic Probe."
European Office Action, dated Nov. 9, 2009, from corresponding European Application No. 07 849 566.0.
Yang, M. M. et al., "High resolution imaging microscope (HIRIM)", Biotechnology et alia, 1998, pp. 1-20.
Yang, M. M. et al., "Graphical user interface for single pixel spectroscopy", Biotechnology et alia, vol. 5, 2000, pp. 1-8.
European Search Report dated Jan. 18, 2012 from correspondent European Application No. 05718903.7.
Misra et al., "Noninvasive Electrical Characterization of Materials at Microwave Frequencies Using an Open-Ended Coaxial Line: Test of an Improved Calibration Technique," IEEE Transactions on Microwave Theory and Techniques, vol. 38, No. 1, Jan. 1990.
Burdette et al., "In Vivo Probe Measurement Technique for Determining Dielectric Properties at VHF Through Microwave Frequencies," IEEE Transactions on Microwave Theory and Techniques, vol. MTT-28, No. 4, Apr. 1980.
Xu et al., "Measurement of Microwave Permittivity Using Open Ended Elliptical Coaxial Probes," IEEE Transactions on Microwave Theory and Techniques, vol. 40, No. 1, Jan. 1992.
Stuchly et al., "Measurement of Radio Frequency Permittivity of Biological Tissues with an Open-Ended Coaxial Line: Part II—Experimental Results," IEEE Transactions on Microwave Theory and Techniques, vol. MTT-30, No. 1, Jan. 1982.
Mosig et al., "Reflection of an Open-Ended Coaxial Line a Application to Nondestructive Measurement Materials," IEEE Transactions on Instrumentation and Measurement, vol. IM-30, No. 1, Mar. 1981.
Hashimshony, U.S. Appl. No. 60/641,081, filed Jan. 4, 2005.
Jan. 7, 2014 Search Report issued in European Patent Application No. 11188221.3.

\* cited by examiner

GRAPHICAL USER INTERFACES (GUI), METHODS AND APPARATUS FOR DATA PRESENTATION

RELATED APPLICATIONS

This application is a Continuation-in-Part of International Application No. PCT/IL2007/001539, filed on Dec. 12, 2007, which in turn claims the benefit under 35 USC 119(e) of U.S. Provisional Application Nos. 60/874,280, filed on Dec. 12, 2006, and 60/914,822, filed on Apr. 30, 2007, all of which are incorporated herein by reference in their entirety.

This application is also a Continuation-in-Part of U.S. Ser. No. 11/745,334 entitled "CLEAN MARGIN ASSESSMENT TOOL" filed on May 7, 2007, which in turn is a Continuation-in-Part of U.S. application Ser. No. 11/743,028 filed on May 1, 2007, currently pending, which is a Continuation-in-Part of U.S. Ser. No. 10/558,831 filed on Nov. 29, 2005, currently pending, which is a National Stage Entry of PCT/IL05/00330, filed Mar. 23, 2005, which in turn claims the benefit under 35 USC 119(e) of U.S. Provisional Application No. 60/555,901 filed on Mar. 23, 2004.

This application is also a Continuation-in-Part of U.S. Ser. No. 11/743,028 entitled "CLEAN MARGIN ASSESSMENT TOOL" filed on May 1, 2007, which is a Continuation-in-Part of U.S. Ser. No. 10/558,831 filed on Nov. 29, 2005, which is a National Stage Entry of PCT/IL05/00330, filed Mar. 23, 2005, which in turn claims the benefit under 35 USC 119(e) of U.S. Provisional Application No. 60/555,901 filed on Mar. 23, 2004.

FIELD OF THE INVENTION

Embodiments of the invention relate generally to graphical user interfaces (GUI), methods and apparatus useful in presentation of data.

BACKGROUND OF THE INVENTION

Considerable research and development has been previously conducted in the fields of tissue characterization, medical imaging and computerized surgical planning and/or guidance. The following listing of reference is presented as being generally indicative of the types of technology known to those of ordinary skill in the art. The list does not purport to be exhaustive.

Variations in electrical impedance of the human tissue are described in the patent literature to provide indications of tumors, lesions and other abnormalities. For example, U.S. Pat. Nos. 4,291,708; 4,458,694; 4,537,203; 4,617,939 and 4,539,640 exemplify systems for tissue characterization by using multi-element probes which are pressed against the skin of the patient and measure impedance of the tissue to generate a two-dimensional impedance map.

Other techniques of this type are described in WO 01/43630 and in U.S. Pat. Nos. 4,291,708 and 5,143,079.

U.S. Pat. Nos. 5,807,257; 5,704,355 and 6,061,589 describe use of millimeter and microwave devices to measure bioimpedance and to detect abnormal tissue. These methods direct a free propagating radiation, or a guided radiation via waveguide, onto the organ. The radiation is focused on a relatively small volume inside the organ, and the reflected radiation is then measured.

U.S. Pat. No. 6,109,270 describes a measurement concept with a multi-modality instrument for tissue identification in real-time neuro-surgical applications.

U.S. Pat. Nos. 6,813,515; 7,082,325 and 7,184,824 U.S. Patent Applications published as 20070255169; 20070179397; 20070032747; 20070032739; 20060264738; 20060253107; 20050021019; 20030187366 and 20030138378 describe tools systems and methods useful in assessing tissue type and/or identifying tumor margins.

U.S. Pat. No. 5,615,132 describes a method and apparatus for determining position and orientation of a movable object using accelerometers.

U.S. Pat. No. 6,833,814 describes an intrabody navigation system for medical applications in which three planar antennas that at least partly overlap are used to transmit electromagnetic radiation simultaneously.

Ascension Technology Corp. (Burlington, Vt., USA) markets a guide for localizing medical instruments with 3D magnetic tracking as "3D Guidance Tm Medsafe".

SUMMARY OF THE INVENTION

A broad aspect of the invention relates to integrating image and/or data (which may be biological, chemical and/or physical data) with planning and/or execution of a procedure. In those embodiments of the invention which are medically oriented, the image data may be, for example, X-ray based (e.g. Fluorography, or computerized tomography [CT]), ultrasound based or magnetic resonance induction (MRI) based. It should be understood that that term "image" used herein refers to data representation indicative of the properties of an examined/measured subject (or substrate) within a region of interest, e.g. tissue region. The examined/measured properties of the subject may include optical, electrical, geometrical characteristics of the subject within the region of interest. The obtained image does not necessarily presents a continuous distribution of the required property or properties all along the region of interest, but in most cases is in the form of a plurality of data pieces corresponding to discrete measurement sites within the region of interest.

According to one aspect of some embodiments of the invention, a graphical user interface (GUI) presents data in meaningful groups to a user. More specifically, the present invention deals with medical data (for example data pertaining to excised tissue) and is therefore described below with respect to this specific application. It should, however, be understood that the invention is not limited to this application and the inventive aspects can be used for various other applications as well. In some exemplary embodiments of the invention, grouped data pertaining to excised tissue is presented to a user in an operating room, optionally during an excision procedure.

According to various embodiments of the inventions, presentation of data for a group includes a collection of individual data and/or one or more statistics which summarize the group.

Another aspect of some embodiments of the invention relates to an apparatus configured and operable to group data pertaining to individual points on a substrate into groups during data acquisition. In some exemplary embodiments of the invention, a user provides input pertaining to group definitions. Optionally, group definitions are selected from a list and/or defined by the user (i.e. "from scratch"). In some exemplary embodiments of the invention, grouped data is presented graphically on a display screen. Optionally, the grouped data is presented superimposed on a representation of the substrate. The representation of the substrate can be, for example a theoretical representation (e.g. a cube), a simplified solid form or an image of the substrate. In medical applications, common imaging modalities include, but are not limited to ultrasound imaging, fluoroscopy, computerized tomography (CT), magnetic resonance induction (MRI), impedance based and other electrical signal based measurements. In some embodiments of the invention, images are prepared concurrently with data acquisition. In other embodiments of the invention, a previously acquired image is employed. In some exemplary embodiments of the invention, decreasing an elapsed time between image acquisition and acquisition of other data to be registered onto an image contributes to an increase in accuracy of registration. Optionally group and/or positional and/or point characterization data is stored in an available memory.

An aspect of some embodiments of the invention pertains to user selection of locations on a substrate for data collection and user grouping of the locations into groups. In some exemplary embodiments of the invention, the user groups the locations into groups using an input device on a hand held data collection probe. Optionally, the substrate includes an excised tissue mass and/or a cavity from which tissue has been excised. In some exemplary embodiments of the invention, user grouping of the locations into groups is indicative of approximate positions of the locations on the substrate.

An aspect of some embodiments of the invention relates to determination of relative position between locations on a substrate and a previously placed marker. Optionally, the marker is placed during image guided localization. In some exemplary embodiments of the invention, a measurement of a relative position between a data collection probe and the marker is made substantially as data is being collected at the location. Optionally, the measurement of relative position can be made by signal strength evaluation and/or signal orientation/polarization and/or use of external position sensors and/or image analysis and/or use of overlapping planar antennas.

An aspect of some embodiments of the invention relates to a hand held device adapted to gather data from a plurality of substrate locations and group the data into user defined groups. Optionally, a user input mechanism on the device allows grouping the data into groups. Optionally, the hand held device is connectable to an external data analysis unit and/or an external vacuum pump. In some exemplary embodiments of the invention, the hand held device is sterilized and/or is provided in sterile packaging.

An aspect of some embodiments of the invention relates to presenting data indicative of substrate status on a model of the substrate. In some exemplary embodiments of the invention, a single probe gathers data on substrate status and position coordinates concurrently. In some exemplary embodiments of the invention, a user indicates a position for each data point. Optionally, the model is a predefined geometric model (e.g. a cube, tube, cylinder or sphere) or a realistic model (e.g. based on a medical image).

An aspect of some embodiments of the invention relates to integration of position data with data indicative of substrate status for planning and/or execution of a procedure on the substrate and/or surrounding material. Optionally, the position data indicates a position of a probe providing the data indicative of substrate status at the time a specific datum is acquired and/or a position of a tool. In medical embodiments of the invention, the tool can be a cutting tool and/or a sampling tool. Optionally, integration of position data with data indicative of substrate status is used in planning and/or execution of a procedure on the substrate and/or surrounding region.

In some exemplary embodiments of the invention, a graphical user interface (GUI) is provided. The GUI includes: (a) a group definition module (software and/or hardware utility) adapted to accept a user input defining groups; (b) a data receiver operable to receive a plurality of individual measurement input datum indicative of status of a substrate; (c) a grouping module (utility) configured to assign each of the individual measurement input datum to one of the groups to produce grouped data; and (d) an output module (utility) adapted to output the grouped data.

In some exemplary embodiments of the invention, an apparatus is provided. The apparatus includes: (a) a probe operable to produce a plurality of individual signal datum indicative of substrate status; (b) a group definition module adapted to accept a user input defining groups; (c) a grouping module configured to receive the signal includes the individual datum and assign each of the individual datum to one of the groups to produce grouped data; and (d) an output module adapted to output the grouped data.

In some exemplary embodiments of the invention, there is provided a method of analyzing a substrate. The method includes: (a) selecting a plurality of locations on a substrate; (b) collecting a datum indicative of substrate status at each of the locations; and (c) grouping the datum into user defined groups.

In some exemplary embodiments of the invention, there is provided a substrate analysis system. The system includes: (a) a substrate position indicator positioned at the substrate; (b) a probe operable to evaluate substrate status and output status indicative datum at individual points; (c) a measurement module configured to determine a relative position of the position indicator and the probe; and (d) a controller adapted to coordinate operation of the probe and the measurement module so that the relative position is determined for each of the individual points.

In some exemplary embodiments of the invention, there is provided a surgical supervision system. The system includes: (a) an input module adapted to receive a path from a procedure planning as described herein; and (b) a guidance system adapted to output guidance instructions to guide a surgical tool in accordance with the path.

In some exemplary embodiments of the invention, there is provided a substrate probe, the probe includes: (a) a data acquisition module adapted to engage a substrate at a user selected point, analyze the substrate and produce a datum indicative of substrate status at the point; (b) a user input device adapted to accept a user input defining groups; and (c) a signal conduit adapted to relay electrical signals.

Optionally, the probe includes a lumen adapted to relay a negative pressure from an external vacuum source to the data acquisition module.

In some exemplary embodiments of the invention, there is provided a substrate probe, the probe includes: (a) a data acquisition module adapted to engage a substrate at a user selected point, analyze the substrate and produce a datum indicative of substrate status at the point; (b) a position determination module adapted to provide a position of the point; (c) a user input device; and (d) a signal conduit adapted to relay electrical signals.

Optionally, the probe includes a lumen adapted to relay a negative pressure from an external vacuum source to the data acquisition module.

In some exemplary embodiments of the invention, there is provided an apparatus for analysis of a substrate. The apparatus includes: (a) a probe operable to produce a plurality of individual signal datum indicative of substrate status at specified locations; (b) a modeling module adapted to produce a three dimensional model of the substrate; (c) a registration module adapted to indicate the specified locations on the model; and (d) an output module adapted to present an indication of substrate status at each of the specified location on the model.

According to various exemplary embodiments of the invention, one or more of the following optional features is included.

Optionally, a registration module is included.

Optionally, the registration module registers the grouped data onto an item selected from the group consisting of a solid representation of the substrate, a space filling model of the substrate and an image of the substrate (e.g. a three dimensional image of the substrate).

Optionally, the user input includes a start command and a stop command.

Optionally, the user input includes a name.

Optionally, the name is indicative of a location on the substrate.

Optionally, the names are presented in nested menus.

Optionally, the individual datum indicative of status of the substrate are linked to position coordinates.

Optionally, the position coordinates are defined relative to the substrate.

Optionally, the output of the grouped data includes the individual datum arranged in groups.

Optionally, the output of the grouped data includes at least one statistic summarizing the individual datum in each of the groups.

Optionally, a memory module adapted to store grouped data output by the output module is included.

Optionally, the data receiver is adapted to receive individual measurement input datum concurrently from an array of probes.

Optionally, the user input is provided at a time selected from before, during and after receipt of the plurality of individual measurement input datum by the data receiver.

Optionally, at least one user input mechanism on the probe is included.

Optionally, at least one indicator on the probe is included

Optionally, the output module includes a display.

Optionally, the output module includes a memory.

Optionally, the probe is adapted to measure dielectric properties of the substrate.

Optionally, the probe is adapted to measure electromagnetic properties of the substrate.

Optionally, the probe is manually operable.

Optionally, the plurality of individual datum indicative of substrate status is correlated to manually selected locations on the substrate.

Optionally, the user input is indicative of a location on the substrate.

Optionally, the probe includes a plurality of sub-probes arranged in a spatial array, the sub-probes collectively operable by a single probe activation signal.

Optionally, the probe is operable in at least two sensing/ characterization modalities.

Optionally, the selecting includes visual inspection.

Optionally, the datum indicative of substrate status includes an evaluation of dielectric properties.

Optionally, the datum indicative of substrate status includes an evaluation of electromagnetic properties.

Optionally, embodiments of the invention include outputting the groups.

Optionally, embodiments of the invention include computing at least one statistic summarizing the individual datum in each of the groups and outputting the at least one statistic.

Optionally, embodiments of the invention include mapping the groups onto a representation of the substrate.

Optionally, the mapping is onto a representation of the substrate selected from the group consisting of a solid representation of the substrate, a space filling model of the substrate and an image of the substrate.

Optionally, the user defined groups are each indicative of a location on the substrate.

Optionally, embodiments of the invention include defining position coordinates for each of the locations on the substrate.

Optionally, the signal originates from the probe and is received at the position indicator.

Optionally, the signal originates from the position indicator and is received at the probe.

Optionally, embodiments of the invention include a position sensor adapted to determine a first probe position and a second substrate position indicator position; wherein the measurement module determines the relative position by comparing the first and second positions.

Optionally, a substrate analysis system according to an exemplary embodiment of the invention includes an imaging module adapted to produce an image depicting the probe and the position indicator; wherein the measurement module determines the relative position from the image.

Optionally, a substrate analysis system according to an exemplary embodiment of the invention includes a registration module adapted to register the status indicative datum from the individual points with medical image data.

Optionally, a substrate analysis system according to an exemplary embodiment of the invention includes a registration module adapted to register local summaries of status indicative datum with medical image data.

Optionally, exemplary embodiments of the invention include a cutting tool mounted on the probe.

Optionally, an exemplary embodiment of the invention includes an output module adapted to output the relative position together with the status indicative datum for each of the individual points.

Optionally, a procedure planning module is included.

Optionally, the procedure planning module is adapted to analyze the output from the output module and calculate a path.

Optionally, the procedure planning module is adapted to accept user input pertaining to a planned path.

Optionally, probes in some embodiments of the invention include a connector to an external data analysis component.

Optionally, probes in some embodiments of the invention are provided as a sterile medical device.

Optionally, the user input device is configured to group the datum into groups of data.

Optionally, a user perceptible indicator of the substrate status is provided on the probe.

Optionally, the user perceptible indicator produces an audible indication.

Optionally, the user perceptible indicator produces a visible indication.

Optionally, some embodiments of the invention are adapted to accept a user input specifying a position of the locations.

Optionally, some embodiments of the invention are adapted to determine a position of the locations.

Optionally, some embodiments of the invention include a position sensor adapted to determine a position of the locations.

Optionally, a model employed by embodiments of the invention includes a predefined geometric model.

Optionally, a model employed by embodiments of the invention includes a realistic model indicative of actual substrate shape.

Optionally, embodiments of the invention are adapted to accept medical image data as an input and generate the realistic model from the medical image data.

Optionally, the output is directed to an item selected from the group consisting of a graphic display, a printer and a memory.

Unless otherwise defined, all technical and scientific terms used herein have the same meaning as commonly understood by one of ordinary skill in the art to which this invention belongs. Although suitable methods and materials are described below, methods and materials similar or equivalent to those described herein can be used in the practice of the present invention. In case of conflict, the patent specification, including definitions, will control. All materials, methods, and examples are illustrative only and are not intended to be limiting.

As used herein, the terms "comprising" and "including" or grammatical variants thereof are to be taken as specifying inclusion of the stated features, integers, actions or components without precluding the addition of one or more additional features, integers, actions, components or groups thereof. This term is broader than, and includes the terms "consisting of" and "consisting essentially of" as defined by the Manual of Patent Examination Procedure of the United States Patent and Trademark Office.

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The term "method" refers to manners, means, techniques and procedures for accomplishing a given task including, but not limited to, those manners, means, techniques and procedures either known to, or readily developed from known manners, means, techniques and procedures by practitioners of architecture and/or computer science.

Implementation of the method and system of the present invention involves performing or completing selected tasks or steps manually, automatically, or a combination thereof. Moreover, according to actual instrumentation and equipment of preferred embodiments of methods, apparatus and systems of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In order to understand the invention and to see how it may be carried out in practice, some embodiments are described, by way of non-limiting example only, with reference to the accompanying drawings. For simplicity and clarity of illustration, elements shown in the figures have not necessarily been drawn to scale. For example, the dimensions of some of the elements may be exaggerated relative to other elements for clarity. Further, where considered appropriate, reference numerals are repeated among the figures to indicate corresponding or analogous elements.

In the drawings:

FIGS. 18A and 18B show the top and cross sectional views, respectively, of a tissue part including a tissue portion under characterization or from which a tissue portion have been removed; and FIG. 18C shows more specifically a peripheral region or surrounding region of said tissue portion;

DETAILED DESCRIPTION OF THE PREFERRED EMBODIMENTS

Overview

Various embodiments of the invention relate to computerized analytic systems, data acquisition tools for use in conjunction with the systems, and user interfaces adapted for data entry and/or data presentation. Specifically, some embodiments of the invention can be used to define and present individual data points in groups and/or to map data to a model of a substrate (region of interest) on which data points reside.

The principles and operation of systems methods and apparatus according to exemplary embodiments of the invention may be better understood with reference to the drawings and accompanying descriptions.

Before explaining at least one embodiment of the invention in detail, it is to be understood that the invention is not limited in its application to the details set forth in the following description. The invention is capable of other embodiments or of being practiced or carried out in various ways. Also, it is to be understood that the phraseology and terminology employed herein is for the purpose of description and should not be regarded as limiting.

Figure 1:
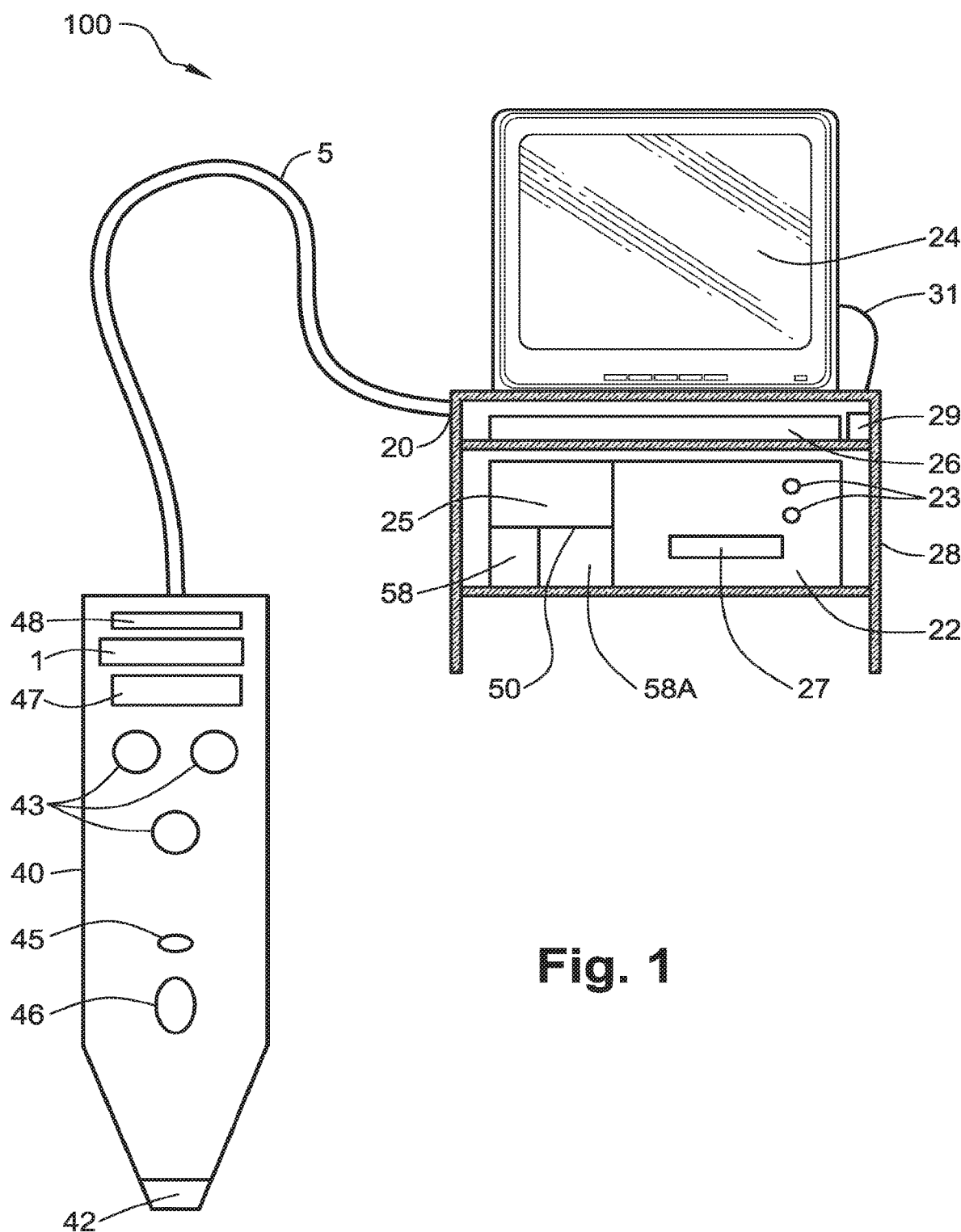
FIG. 1 is a schematic diagram of a system according to one exemplary embodiment of the invention.

FIG. 1 is a schematic diagram of an exemplary system 100 according to one embodiment of the invention. Depicted system 100 includes a data acquisition device or measurement unit (depicted as probe 40). The probe 40 includes an operative portion 42 for scanning the substrate to be measured (contact or contactless scanning), and is configured and operable to measure and/or characterize one or more parameters indicative of one or more conditions or properties of the substrate in the scanned sites thereof.

In some exemplary embodiments of the invention, the substrate is a biological tissue, for example a piece of tissue excised from a subject during a surgical procedure. In other embodiments of the invention the substrate is a mineral substrate, for example a block of material removed from a quarry or mine.

According to various exemplary embodiments of the invention, probe 40 is configured to measure one or more of electromagnetic properties (e.g. using a nonirradiative sensor), dielectric properties, impedance, biological properties, chemical properties, optical properties (e.g. fluorescence emission and/or absorption and/or reflectance of selected wavelengths of light), MRI, energy transmission and/or reflectance (e.g. radio frequency [RF] or microwave [MW]) and temperature (e.g. via infrared thermography). Optionally, probe 40 is configured as a dielectric-property sensor, formed substantially as a coaxial cable.

In some exemplary embodiments of the invention probe 40 includes a single sensor at operative portion 42. In other exemplary embodiments of the invention probe 40 includes an array of sensors at operative portion 42.

In some exemplary embodiments of the invention, operative portion 42 includes a cutting tool and/or a sampling tool. Optionally, the cutting and/or sampling tool is separately controllable. In some exemplary embodiments of the invention, a controller operates the cutting and/or sampling tool responsive to data provided by the sensors.

Optionally, probe 40 includes or is associated with a control utility including inter alia one or more operative memory utilities 47, a main database storage utility 48, one or more control buttons 43 (e.g. for activating probe 40 and/or for initiating and/or measuring/characterization process, as well as a data processing utility (not shown here). Also, probe 40 may include one or more light sources such (depicted as LEDs 45 and 46), an indicator or a display 1 (e.g. an LCD or CRT). In some exemplary embodiments of the invention, display 1 is used to display results and/or information pertinent to diagnosis and/or surgical planning. Optionally, results and/or information from one, two, three or more categories is presented.

There is a tradeoff between the amount of information presented on probe 40 and the ability of a user to organize and comprehend the information. In some exemplary embodiments of the invention, small amounts of information are transiently presented on probe 40 for immediate user evaluation and/or reaction and larger amounts of information are presented for longer periods of time on a display 24 which is physically separate from probe 40.

FIG. 1 depicts a data conduit 5 between probe 40 and an external control station 20. Conduit 5 is drawn as a physical connection (e.g. wires or fiber optic cables) but could be replaced by a wireless link (e.g. Bluetooth, infrared, (IR) or radiofrequency (RF)).

Depicted control station or console 20 includes a control unit 22. The latter is typically a computer system including inter alia one or more control buttons 23 that can be used, for example, to activate probe 40 and/or to initiate and/or control measuring and/or characterization. Optionally, control station 20 includes an additional input interface, such as a keyboard 26 or joystick 29 and/or a read/write device 27 (e.g. CD ROM or DVD drive) and/or a storage unit 50. Storage unit 50 can include a data processor or processing unit. Optionally, control unit 22 may be configured to communicate with a signal analyzer 25 and/or an audio speaker 31 and/or a display screen 24.

Control station 20 is depicted on a rack 28 although it could be incorporated into a hand-held device (e.g. personal digital assistant or smart-telephone) or a laptop computer.

Optionally, processing unit 50 includes a probe location module 58 and/or a physical marking module 58a.

Exemplary probes and analytic systems useful in the context of various embodiments of the present invention, (e.g. for sensing, receiving, processing, storage and/or display) are described in U.S. Pat. No. 6,813,515 entitled "Method And System For Examining Tissue According To The Dielectric Properties Thereof" filed on Jan. 4, 2002 and U.S. Pat. No. 7,505,811 entitled "Method and apparatus for examining tissue for predefined target cells, particularly cancerous cells, and a probe useful in such method and apparatus" filed on Nov. 18, 2002 and US 2006/0253107 entitled "Clean Margin Assessment Tool" filed on Mar. 23, 2005 and US 2007/0179397 entitled "Methods, Systems, And Sensors For Examining Tissue According To The Electromagnetic Properties Thereof" filed on 12 Feb. 2007, each of which are assigned to the common assignee of the present invention and each of which are hereby incorporated by reference.

Location module 58 and physical marking module 58a optionally employ technology described, for example, in U.S. Pat. No. 7,082,325 filed on Jul. 15, 2004 entitled "Method And Apparatus For Examining A Substance, Particularly Tissue, To Characterize Its Type".

In some exemplary embodiments of the invention, location module 58 relies upon medical imaging data. Medical imaging data includes, but is not limited to X-ray (e.g. fluorography or computerized tomography [CT]), magnetic resonance induction (MRI), ultrasound (US) and infrared (IR) imaging data.

Briefly, marking module 58a issues a command to physically mark a measured location on the substrate in response to an instruction from processing unit 50.

In some exemplary embodiments of the invention, the command causes deployment of a detectable material from operative portion 42 of probe 40 to physically mark a measurement location. Detection of the physical marking can be immediate or delayed by the user. Physical marking may be performed for example by using a visually detectable substance (e.g., one or more color biological marking ink, emitted from a jet nozzle mounted at operative portion 42 of probe 40.

The processing unit analyzes a measurement from probe 40. After substrate (e.g. tissue) recognition has been performed, marking module 58a issues a color specific command to a jet nozzle (not pictured) and an appropriate color mark is printed on the substrate. According to some embodiments of the present invention, the one or more measurements in a region or area, e.g. which relate to the measurement outputs of the measured region or area, may be marked by using for example the marking module 58a. The marking may correspond to the substrate characterization result/output and/or to region related data and/or to other data available from the processing unit 50.

According to various embodiments of the invention, probe 40 may be configured as an extracorporeal device, an intracorporeal device, a device adapted for use on a portion of subcutaneous tissue, or a device adapted for use on a portion of an intracorporeal tissue during an open surgery.

Exemplary intracorporeal devices can be specifically configured for minimally invasive surgery and/or insertion via a trocar valve and/or for insertion via a body orifice to a body lumen (e.g. for use on a portion of inner lumen wall for further penetrating the lumen for use on a portion of an intracorporeal tissue outside the lumen) and/or for percutaneous insertion to a body lumen (e.g. for use on a portion of inner lumen wall for further penetrating the lumen for use on a portion of an intracorporeal tissue outside the lumen).

External display screen 24 and indicator 1 on probe 40 can be, for example CRT screens, LCD screens, plasma screens or projector displays or any other device capable of providing image or other data (e.g. audible output). In an exemplary embodiment of the invention, various categories of information are displayed in a compartmentalized user interface (e.g. Windows©, Linux© or Mac OS©). Optionally, multiple monitors may be used to display the data.

Exemplary Graphical User Interface

Figure 14:
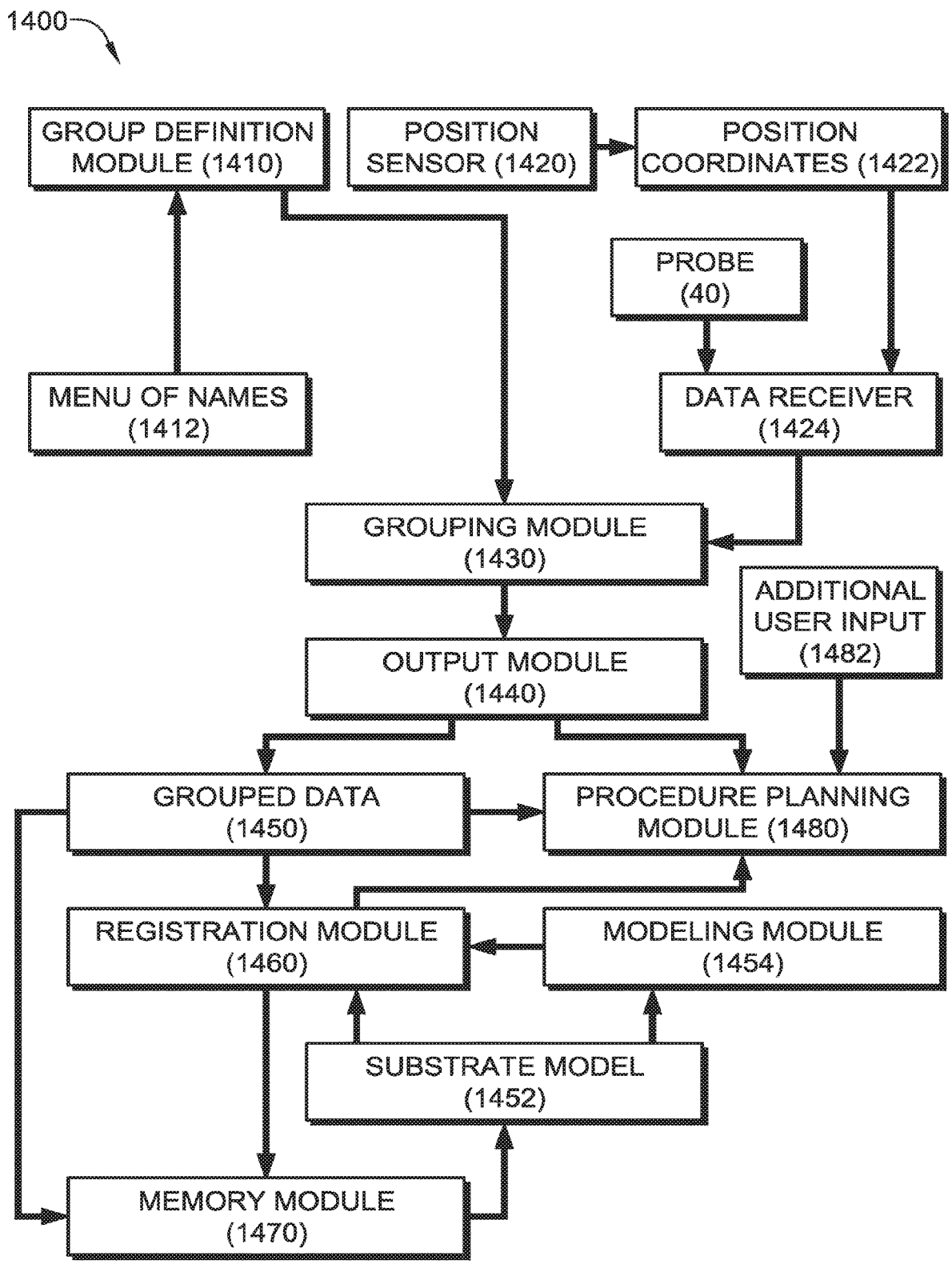
FIG. 14 is a schematic representation of an exemplary graphical user interface according to an embodiment of the invention.

FIG. 14 is a schematic block diagram illustrating interaction of components of exemplary graphical user interfaces (GUIs) 1400 according to some embodiments of the invention. FIGS. 2A, 2C, 2E, 2F, 2G, 2H, 3A and 3B depict exemplary graphic output from a GUI of this type.

In some exemplary embodiments of the invention, GUI 1400 includes a group definition module 1410 adapted to accept a user input defining groups and a data receiver 1424 operable to receive a plurality of individual measurement input datum indicative of status of a substrate (e.g. from probe 40).

In some exemplary embodiments of the invention, the user input comprises a start command and a stop command. Optionally, the group definition module includes a single button and a first press of the button indicates "begin assigning measurement input datum to a group" and a second click of the button indicates "last measurement input datum received was the end of a group". In some embodiments of the invention, each click of the button after the first click indicates both an end of a preceding group and a beginning of a subsequent group. In some exemplary embodiments of the invention, the button is positioned on probe 40.

In some exemplary embodiments of the invention, the user input comprises a name. Optionally, the name can be selected from a menu (e.g. using a physical interface such as a scroll wheel, mouse or joystick) or entered manually by the user (e.g. using a keyboard or via a voice command).

Optionally, the name is indicative of a general location on the substrate. In some exemplary embodiments of the invention, group names are according to a commonly used convention among medical practitioners: Medial (M), Lateral (L), Posterior/Deep (D), Anterior/Superficial (SF), Inferior (I) and Superior (S). Optionally, multiple groups may be assigned to a same general location (e.g. S1, S2 or M1, M2 and M3).

In some exemplary embodiments of the invention, an interior surface of a body cavity serves as the substrate. Optionally, data collected from the cavity is used by append "C" or "CAV" to group names of the commonly used convention described above. Optionally, data is collected from an excised tissue and a cavity resulting from the excision in a single procedure.

Optionally, group numbers are used in place of names. In some exemplary embodiments of the invention, groups are successively numbered in their collection order.

In some exemplary embodiments of the invention, names are presented to a user in nested menus.

Optionally, a user selects a group name from a list of names, optional names descriptive of regions.

Optionally, the user enters names without using a list, for example by using keyboard 26 or buttons 43 on probe 40 the user may name region 210 'XL'. Alternatively or additionally, the user may store the name 'XL' in a 'language' database for example at database storage unit 48.

In some exemplary embodiments of the invention, groups are named by pressing control buttons 43 and 44, or the keyboard 26 and/or by a voice operating system or machine and/or by using a touch screen and/or a virtual touch screen (e.g., by relating movements and gestures of the surgeon hands for operations on the screen).

The user input defining groups and individual measurement input datum are processed by a grouping module 1430 configured to assign each of said individual measurement input datum to one of said groups to produce grouped data 1450 for output via an output module 1440.

Optionally, GUI 1400 includes a registration module 1460. In some exemplary embodiments of the invention, registration module 1460 registers grouped data 1450 onto a substrate model 1452. Registration can be based upon general positional information (e.g. as indicated by a group name) and/or on position coordinates for one or more points in a group. Substrate model 1452 can be, for example, a geometric solid representation of the substrate (e.g. a cube, sphere, cylinder, tube or polyhedral solid), a space filling model of the substrate (e.g. a model based upon general characteristics of an anatomic feature or organ being examined) or an image of the substrate produced using any known imaging technology. Optionally, registration to an image can be to a previously acquired image.

In some exemplary embodiments of the invention, individual datum indicative of status of said substrate are linked to position coordinates. Optionally, the position coordinates are defined relative to the substrate. One exemplary way to accomplish this is to use a position sensor 1420 to generate position coordinates 1422 to be transmitted to data receiver 1424 together with individual measurement input datum from probe 40. Optionally, position sensor 1420 is mounted on probe 40.

Figure 2A:
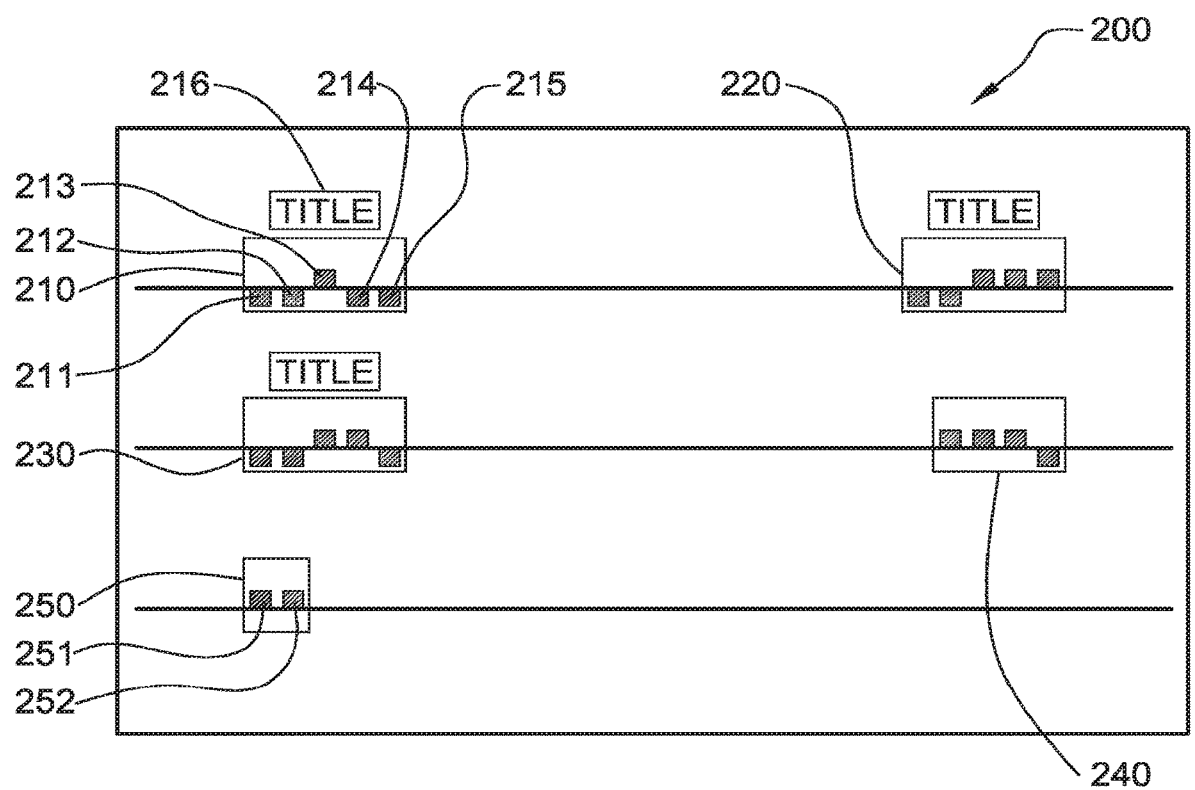
FIG. 2A is a schematic of an exemplary information screen according to an embodiment of the invention.

FIG. 2A is a schematic representation of an exemplary output 200 of grouped data 1450 from GUI 1400. Output 200 can be displayed, for example, on display screen 24 and/or indicator 1, e.g. the LCD and/or stored in a memory of processor 50 and/or written to a machine readable media in read/write drive 27. In some exemplary embodiments of the invention, output 200 displays information in a way designed to assist a user in making a diagnosis and/or planning a surgical response.

Depicted exemplary output 200 includes groups of measurements or results 210, 220, 230, 240 and 250. Optionally, each group corresponds to a region on the substrate. Groups may include one or more measurements or results and different groups can include different numbers of measurements/results.

For example region 210 includes five measurements outputs, e.g. measurements 211, 212, 213, 214 and 215, while region 250 includes two measurements outputs 251 and 252.

According to some embodiments of the invention, a single measurement relates to a single point on a substrate (e.g. a mass of excised tissue) and a group of measurements relates to an area or general location on the substrate where all the single measurements in the group were performed.

Figure 2B:
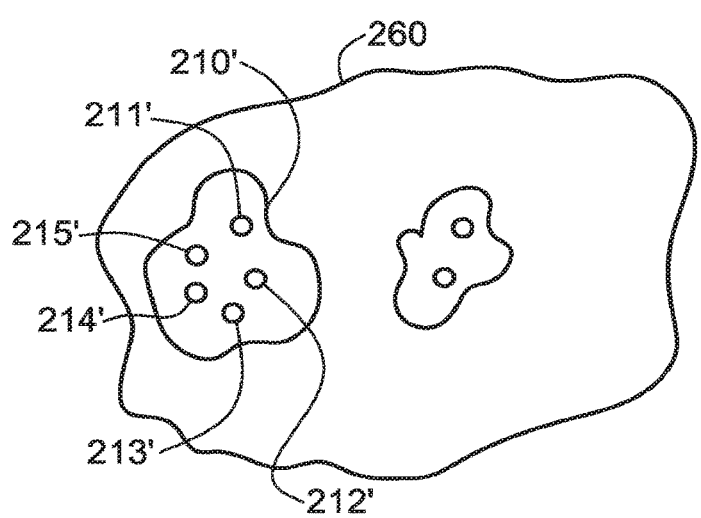
FIG. 2B is an exemplary schematic representation of a substrate according to one embodiment of the invention.

For example, as shown in FIG. 2B, a user may examine an area 210' on substrate 260. The area 210' may be displayed in output 200 as group 210. The measurement output of each examined point in area 210', e.g. points 211', 212', 213', 214' and 215', may displayed, respectively, in region 210 for example as bars 211, 212, 213, 214 and 215 of FIG. 2A. Correlation between group 210 and area 210' is optionally provided by a descriptive title 216 or group name (e.g. L for lateral).

Optionally, each group is automatically named or numbered. For example the first region which was examined e.g. region 210 is numbered "One" and the following examined region is automatically numbered "Two". In some embodiments, the user may insert a title (e.g. name or number) to each region, for example according to the location of the region in the examined substance, or according to the number of examination.

According to some embodiments of the invention, a single measurement may be related to a single point on a substrate, such as a tissue, which was measured or characterized by a single sensor. Optionally, the sensor is one of a group of sensors provided in an array on operative portion 42 of probe 40.

According to other embodiments of the invention, a single measurement may be related to a plurality of points on a substrate measured by individual sensors belonging to a group of sensors provided in an array on operative portion 42 of probe 40. Optionally, the single measure is an arithmetic mean or median of a range of measurements. Optionally, an indication of variability is also provided.

In those embodiments of the invention which employ a group or array of sensors, the group or array is optionally operated in concert. Operation in concert refers to concurrent or sequential measurements performed by individual sensors in the group/array as a result of a single operation input or command. In some exemplary embodiments of the invention, use of groups or arrays of sensors contributes to an increase in accuracy and/or reliability of collected data without extending data collection time.

For example, as shown in FIG. 2B, a surgeon may attach the probe 40 to the area 210' on substance 260. If operative portion 42 of probe 40 includes an array of sensors, each point in area 210' may be presented as a single datum indicative all measurements from all sensors in the array or as a series of data outputs (one output for each sensor in the array). Additionally, one or more measurement outputs of area 210' may be displayed on the information screen 200 using for example the display screen 24 or the indicator 1, e.g. the LCD.

Figure 2C:
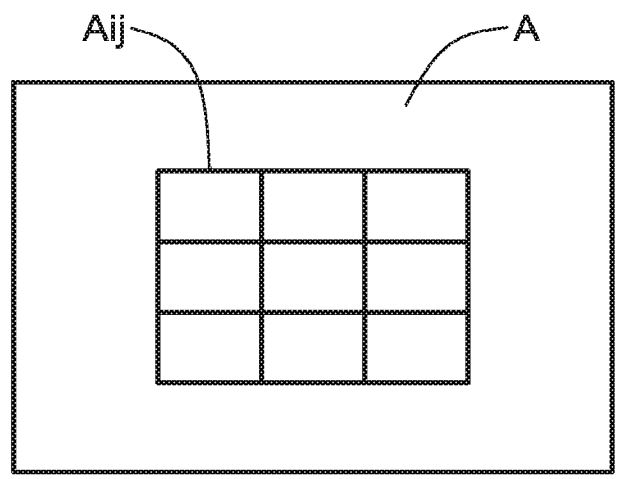
FIG. 2C is a schematic of an exemplary information screen according to an embodiment of the invention.
Figure 2D:
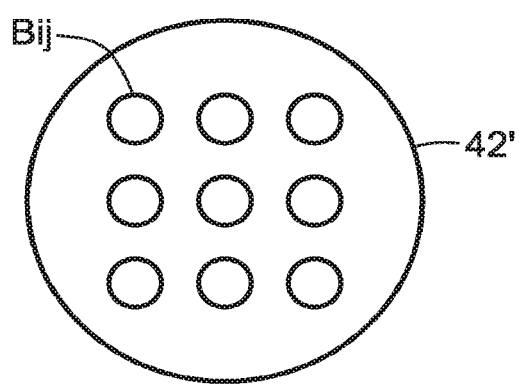
FIG. 2D is a diagram of an exemplary probe array according to some embodiments of the invention.

FIG. 2C depicts an exemplary matrix A of outputs of a sensor array 42' (FIG. 2D).

In some exemplary embodiments of the invention a matrix A is presented for each of examined points 211', 212', 213', 214' and 215' in area 210'. According to these exemplary embodiments of the invention, individual measurements are displayed concurrently with each index $A_{ij}$ in matrix A representing respectively an output from a single measurement by the corresponding sensor $B_{ij}$ of sensor array 42'.

In other exemplary embodiments, measurements from sensor array 42' are condensed into a single datum (e.g. by averaging) for each of examined points 211', 212', 213', 214' and 215' in area 210'.

Alternatively or additionally, a data group (e.g. 210) includes multiple measurement outputs of Matrix A resulting from multiple operations of array 42' at multiple locations. For example the user may characterize a first substrate area (e.g. 211') using probe 40 with a sensor array 42' and a second substrate area (e.g. 214' or adjacent to the first area) by moving the senor array. For example, measurement outputs 211 of the first substrate area and 214 of the second substrate area are in the form of matrix A, and the group presentation 210 is a sequence of matrices A. Optionally, measurement outputs of the first substrate area and the second substrate area may be displayed as a single group (e.g. "M") or as separate groups (e.g. M1 and M2). Optionally, several probes including matrices are operated in parallel. In some exemplary embodiments of the invention, use of matrices reduces data collection time and/or contributes to an increase in meaningfulness of grouped data.

According to various embodiment of the invention, a single measurement output can be binary (e.g. yes/no or malignant/clear), discrete (e.g. on a scale with numbered units, optionally represented by symbols that increase in size incrementally) or continuous (e.g. a temperature, a conductivity, a color selected from a spectrum)

According to various embodiments of the present invention, a measurement output level or percentage of, for example a cancerous or non-cancerous substance (e.g. a substrate tissue) is displayed digitally (e.g. no/yes or red/green), or as a bar (e.g. the cancerous or non-cancerous level or percentage may be indicated according to a bar length, or color and/or position with respect to a baseline), a circle which is filled proportionally, as a combination of digital result and a bar, and only as a level result, e.g. including only the cancerous level without a yes or no indication.

Optionally, a faulty measurement e.g. faulty sensor signal, mechanical failure of the probe is indicated on the GUI, e.g. designated by an empty box and/or by a dedicated color and/or an error message.

Figure 2E:
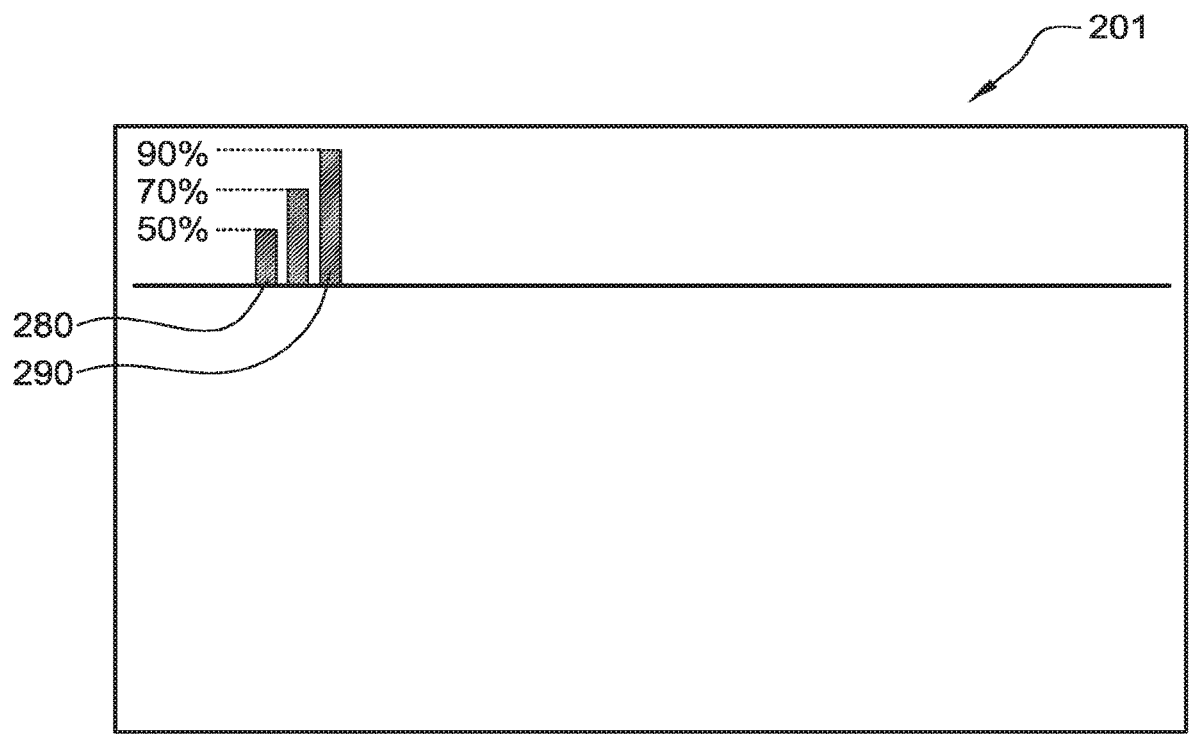
FIGS. 2E to 2H are schematics of additional exemplary information screens according to embodiments of the invention.

FIG. 2E depicts an additional exemplary display screen 201 with bars 280 and 290 with lengths represent a cancerous percentage, (50% and 90% respectively) measured during a single measurement.

Optionally, individual measurement datum and/or group names are stored in system 100 (e.g. in control station 20 or in database storage unit 48 of probe 40).

According to some embodiments of the invention, each measurement datum acquired by probe 40 is summarized by a transient audio indication. For example, a beep may be used to indicate "normal" and a buzz may be used to indicate "abnormal" substrate status. A sequence of beeps may be used to indicate a faulty measurement Alternatively or additionally, a status of grouping module 1430 may be indicated by audio signals. For example delivery of a "start" signal from group definition module 1410 can produce a single click which indicates that subsequently acquired individual datum will be grouped together and delivery of a "stop" signal from group definition module 1410 can produce a double click which indicates an end to grouping.

According to some embodiments of the present invention, each measurement datum acquired by probe 40 is summarized by a transient visual indication. For example, using the light sources 45 and 46 (e.g. red LED indicates abnormal measurement, green LED indicates normal measurement, yellow LED indicates a faulty measurement).

Figure 2F:
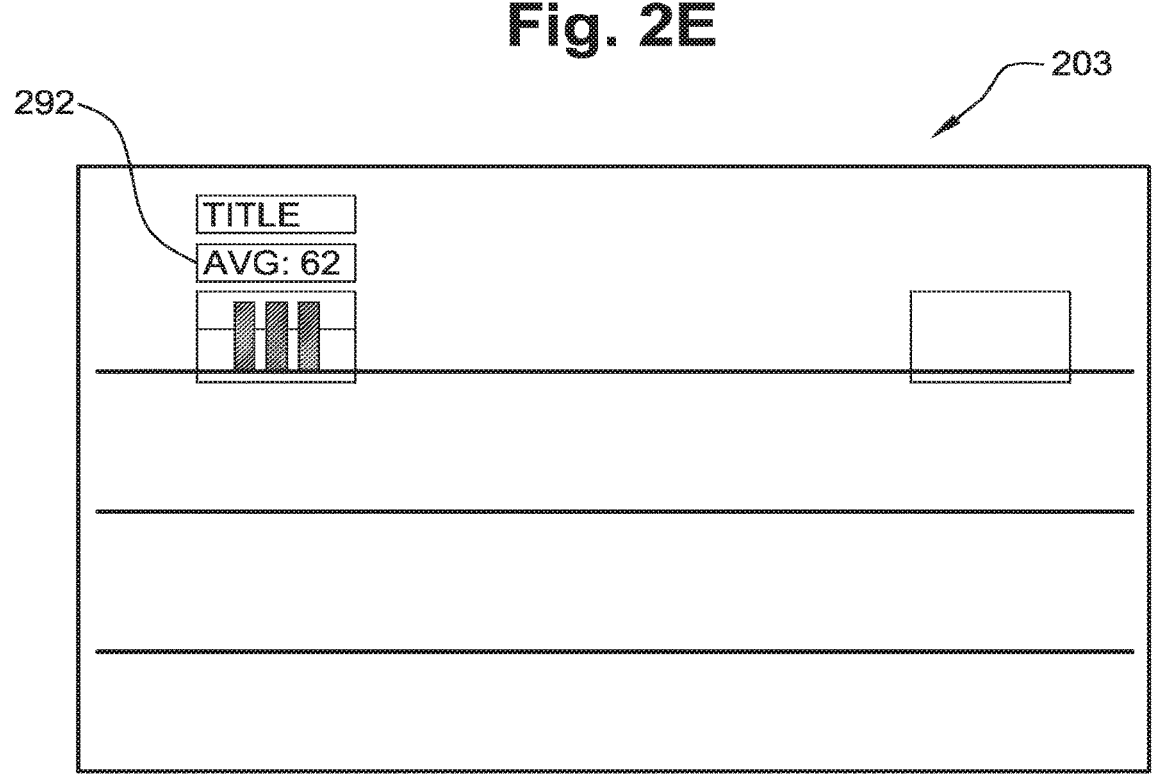

FIG. 2F depicts an additional exemplary display screen 203 featuring exemplary output of a summary statistic 292 (e.g. average) for grouped data 1450. Summary statistic 292 can be presented instead of, or in addition to, individual bars representing status indicative data from individual locations.

Types of summary statistic 292 include, but are not limited to mean average, mode, median, standard error of the mean (SEM) and standard deviation (SD). Optionally, two or more summary statistics are displayed concurrently (e.g. mean and SD or median, mean and SEM). Optionally, a total measurement output 292 for each region may be displayed separately. The total measurement output 292 represents the total of all the measurements performed in the region.

In some exemplary embodiments of the invention, summary statistic 292 indicates a number of datum in the group with a value exceeding a predefined threshold, a peak or an integral of all measurements in the group.

In some exemplary embodiments of the invention, summary statistic 292 is presented during data acquisition and is updated as new data is added to the group.

In some exemplary embodiments of the invention, summary statistic 292 is presented when data acquisition ends and the group is closed.

Figure 2G:
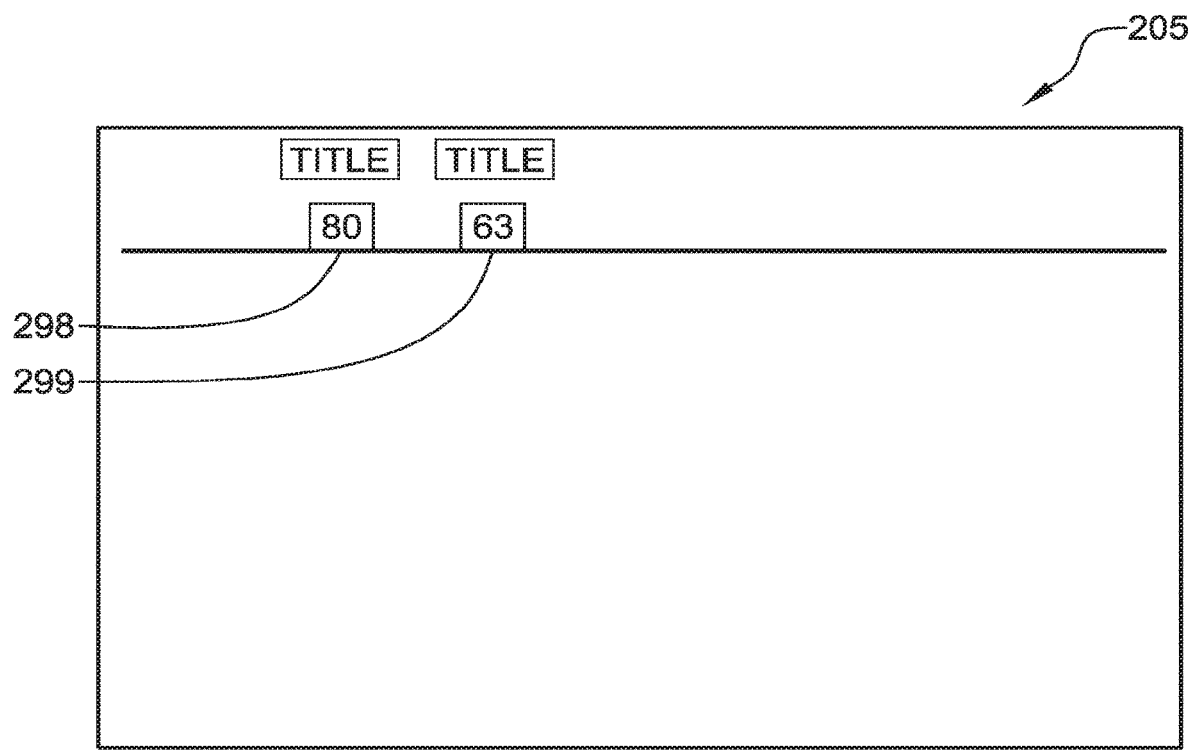

FIG. 2G depicts an additional exemplary display screen 205 showing measurements outputs 298 and 299 including an alpha numeric measurement indication.

Figure 2H:
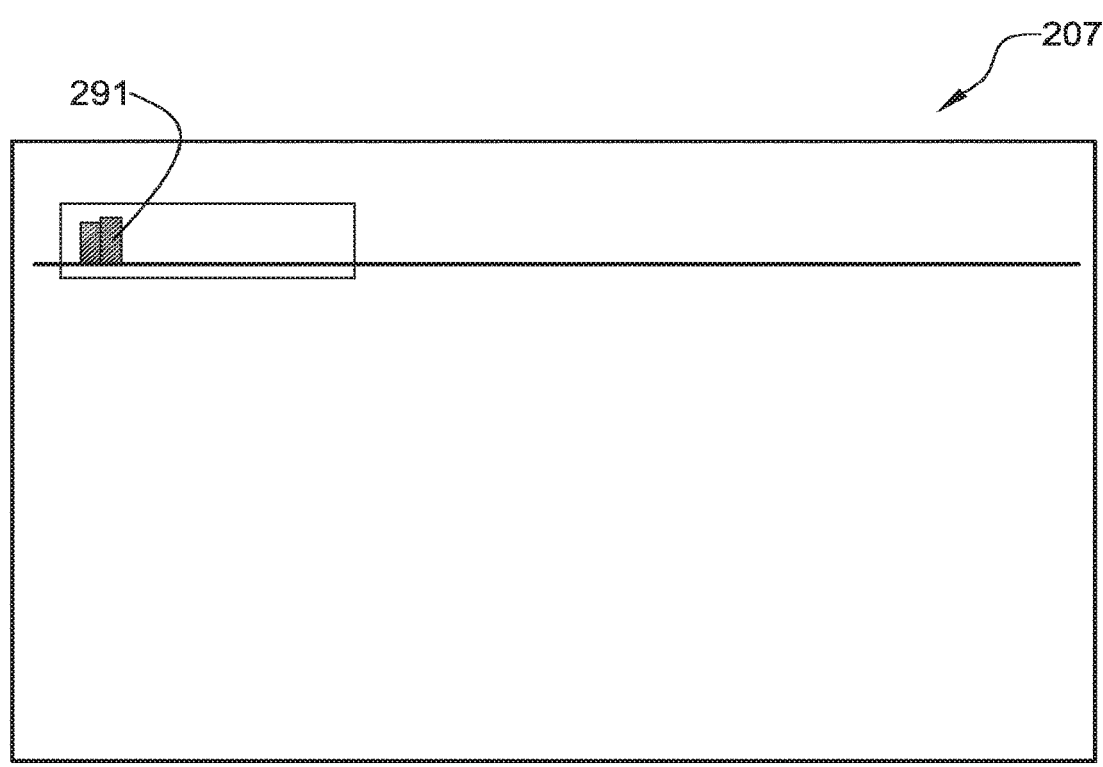

FIG. 2H depicts concurrent display 291 of data from two different sensor types as described in detail hereinbelow.

As described hereinabove, output of grouped data 1450 comprises individual datum arranged in groups and/or at least one statistic summarizing the individual datum in each of the groups. Optionally, grouped data 1450 is stored in a memory module 1470.

In some exemplary embodiments of the invention, data receiver 1424 is adapted to receive individual measurement input datum concurrently from an array of probes. Alternatively or additionally, data receiver 1424 is adapted to receive individual measurement input datum concurrently from sensors of different types.

According to various exemplary embodiments of the invention, user input is provided at before and/or during and/or after receipt of said plurality of individual measurement input datum by data receiver 1424.

Exemplary Apparatus for Substrate Analysis

In some exemplary embodiments of the invention, system 100 (FIG. 1) includes an apparatus for analysis of a substrate. The apparatus may be operable for determining whether a clean margin of healthy tissue exists around a malignant tumor or abnormal tissue. This will be exemplified further below with reference to FIGS. 18A-18B, 19A-19B, 20 and 21A-21B. According to these embodiments of the invention, the apparatus includes probe 40 operable to produce a plurality of individual signal datum indicative of substrate status. Optionally, probe 40 is activated by contacting an operative portion 42 with a portion of the substrate and/or by operation of one or more control inputs 43. The apparatus includes group definition module 1410 (FIG. 14) adapted to accept a user input defining groups and grouping module 1430 configured to receive said signal datum indicative of substrate status and assign each of said individual datum to one of said groups to produce grouped data 1450 and an output module 1440 adapted to output grouped data 1450. According to various embodiments of the invention, output module 1440 includes a display (e.g. 1 and/or 24) and/or memory (e.g. 27 or 50) and/or printer (not depicted). In some embodiments of the invention, components such as group definition module 1410 and/or grouping module 1430 and/or output module 1440 are provided on probe 40.

In some exemplary embodiments of the invention, apparatus 100 includes one or more user input mechanism(s) on probe 40. In the embodiment depicted in FIG. 1, buttons 43 on probe 40 function as user input mechanisms.

Optionally, apparatus 100 includes at least one indicator on probe 40 (e.g. LEDs 45 and 46). These indicators function as part of output module 1440.

In some exemplary embodiments of the invention, probe 40 measures dielectric and/or electromagnetic properties or other properties of said substrate as described hereinabove. Probes capable of measuring dielectric and/or electromagnetic properties or other properties have been described and one of ordinary skill in the art will be capable of adapting them for use in the context of the invention.

In some exemplary embodiments of the invention, probe 40 is manually operable (e.g. by button press and/or by contact with substrate).

In some exemplary embodiments of the invention, a plurality of individual datum indicative of substrate status (e.g. 211, 212, 213, 214 and 215) is correlated to manually selected locations on the substrate (211', 212', 213', 214' and 215'; See FIGS. 2A and 2B).

In some exemplary embodiments of the invention, the apparatus comprises a registration module 1460. Optionally, registration module 1460 registers the grouped data onto a model of the substrate. According the various embodiments of the invention, the model can be a solid representation of the substrate (e.g. a cube, sphere, dodecahedron or cylinder) and/or a space filling model of the substrate and/or an image of the substrate.

In some exemplary embodiments of the invention, user input is indicative of a location on said substrate. For example, group names entered via group definition module can be used to indicate which flux of a cube grouped 1450 should be displayed upon.

Figure 3A:
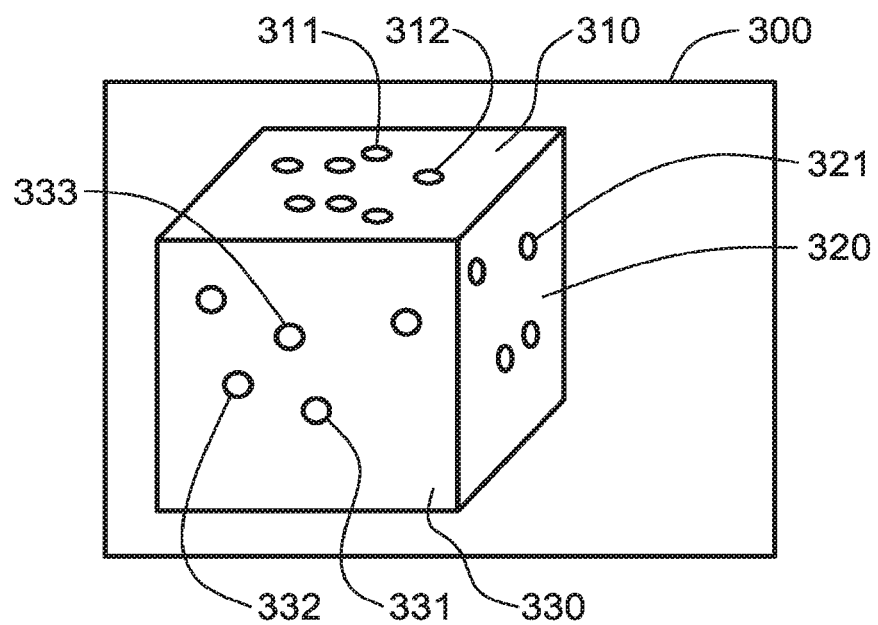
FIG. 3A is a schematic diagram of registration of output data onto a pre-defined geometric model according to an exemplary embodiment of the invention.

FIG. 3A shows an exemplary output 300 of grouped data registered onto a three dimensional model. In the figure, the substrate is represented as a cube. Faces 310, 320 and 330 of the cube are visible. During examination of a substrate (e.g. an excised tissue mass) a user optionally selects an automatic region selection mode display. For example the user may measure substrate characteristics at points on different regions of the substrate (e.g. [311, 312] and [321] and [331,332 and 333]) where the square brackets indicate group designations supplied by the user via group definition module 1410.

In some exemplary embodiments of the invention, registration module 1460 applies grouped data 1450 to substrate model 1452 to produce an output of the type depicted in FIG. 3A. In the depicted exemplary output, substrate model 1452 is in the form of a cube, where each surface of the cube corresponds to a region of the cube according to the according to the M/L/D/SF/I/S nomenclature system described above.

In other exemplary embodiments of the invention, three dimensional shapes other than a cube are used as substrate model 1452 (e.g. sphere, dodecahedron, tube or cylinder.)

When shapes other than a cube are used, appropriate naming systems can be employed. For example, a spherical model can employ names based on longitude and/or latitude. A tubular or cylindrical model can employ names based on z (e.g. top, top-center, center, center-bottom, and bottom) and angle in plane perpendicular to z. For polyhedral shapes (e.g. dodecahedron) names can correspond to enumeration of faces in a predetermined order (e.g. 12 in the case of a dodecahedron), which may further be refined if the polyhedron has a specific symmetry (e.g. in the case of 6 face polyhedron: a cube, a box, a pyramid; each enable a more specialized enumeration)

Figure 3B:
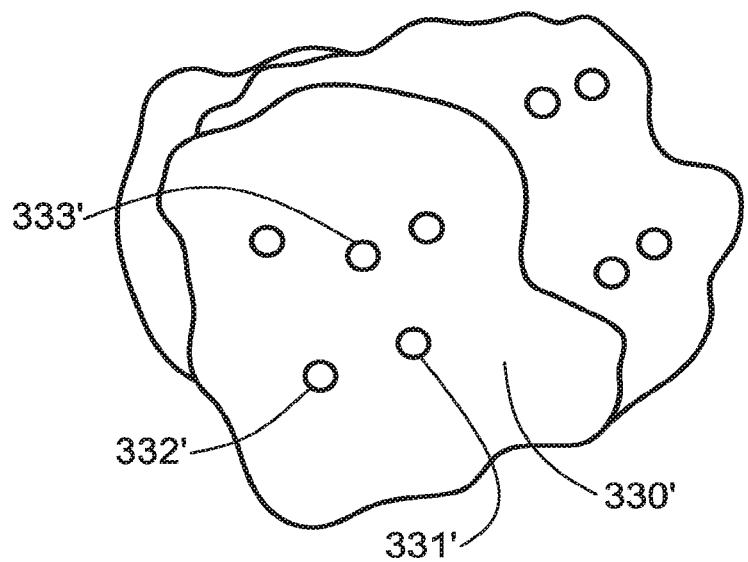
FIG. 3B is a schematic diagram of a three dimensional substrate according to an embodiment of the invention.

FIG. 3B shows an irregularly shaped substrate with a surface 330' corresponding to face 330 of the cube model of FIG. 3A. Locations 331', 332' and 333' indicate sites of measurements 331, 332 and 333 respectively.

Although a simple substrate model 1452 is depicted in FIG. 3A, display 300 can include a model 1452 in the form of medical image data. Medical image date can include any imaging data, including image data types mentioned hereinabove. Optionally, the image data may is pre-acquired or acquired concurrent with acquisition of individual datum indicative of substrate status.

In some exemplary embodiments of the invention, individual datum indicative of substrate status belonging to a same group are displayed registered on substrate model 1452 with a sign (e.g. group indicator) or form (e.g. color) to aid the user in identifying which points belong to groups indicative of which substrate regions. Optionally, individual datum indicative of substrate status of all points in a first region may have a first sign or symbol such as a star and/or color such as orange and individual datum indicative of substrate status of all points which relate to a second region may include a second symbol such as a circle and/or a second color such as black. In some exemplary embodiments of the invention, the M/L/D/SF/I/S nomenclature is linked to specific symbols and/or colors. Optionally, the letters M/L/D/SF/I/S are used as symbols for the corresponding faces of the cube. Alternatively or additionally, colors are assigned to the six faces of the M/L/D/SF/I/S system (e.g. M—red, L—orange, D—yellow, SF—green, I—blue, S—violet).

Alternatively or additionally, each displayed individual datum indicative of substrate status includes data relating to substrate status using different formats as described in detail hereinabove. Alternatively or additionally, summary statistics 292 as described hereinabove are displayed on each face. Optionally, the summary statistics 292 summarize a singe group or all groups belonging to a particular face. Optionally, summary statistic is color coded or marked with a symbol as described above for individual datum.

According to some embodiments of the present invention individual datum indicative of substrate status belonging to a same group and/or residing on a same face are connected by a connector. Optionally, the connector is as a surface area connector enclosing all individual datum belonging to the group. Optionally, the connector is added automatically, for example by registration module 1460 and/or grouping module 1430. The connector can be, for example, a graphical indication of the relation between points. The graphical indication can include one or more of a line connecting the individual datum locations, a counter enclosing all the individual datum locations or a geometric shape contacting the individual datum locations. In some exemplary embodiments of the invention, the connector is dynamic, and is updated as additional points belonging to the group are added. Updating can be fully automatic or in response to an update command.

In some exemplary embodiments of the invention, individual datum indicative of substrate status are linked to position coordinates. Exemplary means of acquiring position coordinates are described hereinbelow.

Optionally, operative portion 42 of probe 40 includes a plurality of sub-probes arranged in a spatial array as described above with reference to FIGS. 2C and 2D. In some exemplary embodiments of the invention, the sub-probes are collectively operable by a single probe activation signal. Optionally, contact with the substrate serves as a probe activation signal. In some exemplary embodiments of the invention, output of a group of sensors arranged in an array is used to provide a local summary of substrate status.

In some exemplary embodiments of the invention, probe 40 is operable in at least two modalities. For example, concurrent sensing and detection of electric impedance (EI) and magnetic resonance (MR) properties can be performed by operative portion 42 of probe 40. Optionally, sensors for two or more modalities are integrated into one sensing head.

In some exemplary embodiments of the invention, different sensing modalities are combined to produce a third "hybrid" modality. For example, concurrent measurement of EI properties of a specific region of the substrate and measurement of MR properties of the same substrate region produces a hybrid mode indicative of induced change in EI properties due to MR absorption of the incident electromagnetic radiation pulse.

Exemplary Substrate Analysis Method

Figure 15:
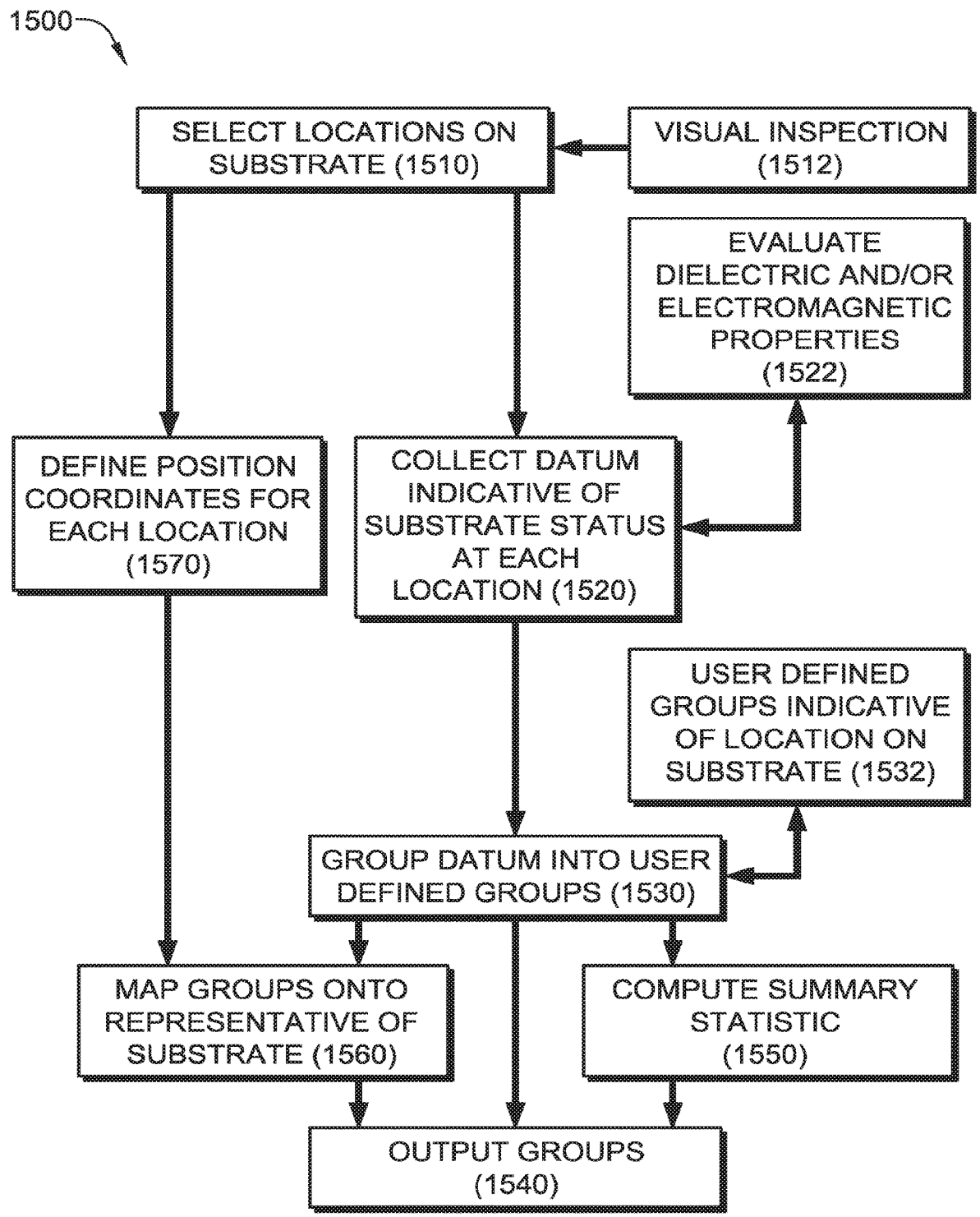
FIG. 15 is a simplified flow diagram of a method according to an exemplary embodiment of the invention.

FIG. 15 is a simplified flow diagram of an exemplary method 1500 of analyzing a substrate. Depicted exemplary method 1500 includes selecting 1510 a plurality of locations on a substrate collecting 1520 a datum indicative of substrate status at each location and grouping 1530 the data into groups defined by a user. Optionally, selecting 1510 is at least partially based upon visual inspection 1512 of the substrate by the user. According to some exemplary embodiments of the invention, datum indicative of substrate status reflect an evaluation 1522 of dielectric properties and/or electromagnetic properties of the substrate at each selected location.

According to method 1500, the user is presented with an output 1540 of the groups. In some exemplary embodiments of the invention, output of the data in groups contributes to an ability of the user to make a decision. Optionally, the decision relates to diagnosis and/or surgery. According to various embodiments of method 1500, output 1540 can be to a digital display (e.g. LCD or CRT screen) and/or printer and/or memory. The output can optionally include one or more additional features described below. Additional features can aid the user in making the decision.

In some exemplary embodiments of the invention, grouping 1530 is followed by computation 1550 of one or more summary statistics as described hereinabove. Optionally, the summary statistic is output 1540 in addition to, or as an indication of, group data.

In some exemplary embodiments of the invention, method 1500 includes mapping 1560 groups onto a representation of the substrate. Optionally, mapping 1560 is based upon definition 1570 of position coordinates for each location (as explained hereinbelow) and/or on user defined groups indicative of location 1532 (as explained hereinabove).

As explained hereinabove, mapping 1560 can be onto any representation of the substrate including but not limited to a polygonal solid representation of the substrate, a space filling model of the substrate and an image of the substrate.

Exemplary System with Mapping Capabilities

In some exemplary embodiments of the invention, a substrate analysis system of the general type depicted in FIG. 1 as system 100 is modified with a position co-ordinate measurement module for determining position coordinates of the locations on the substrate.

Figure 4A:
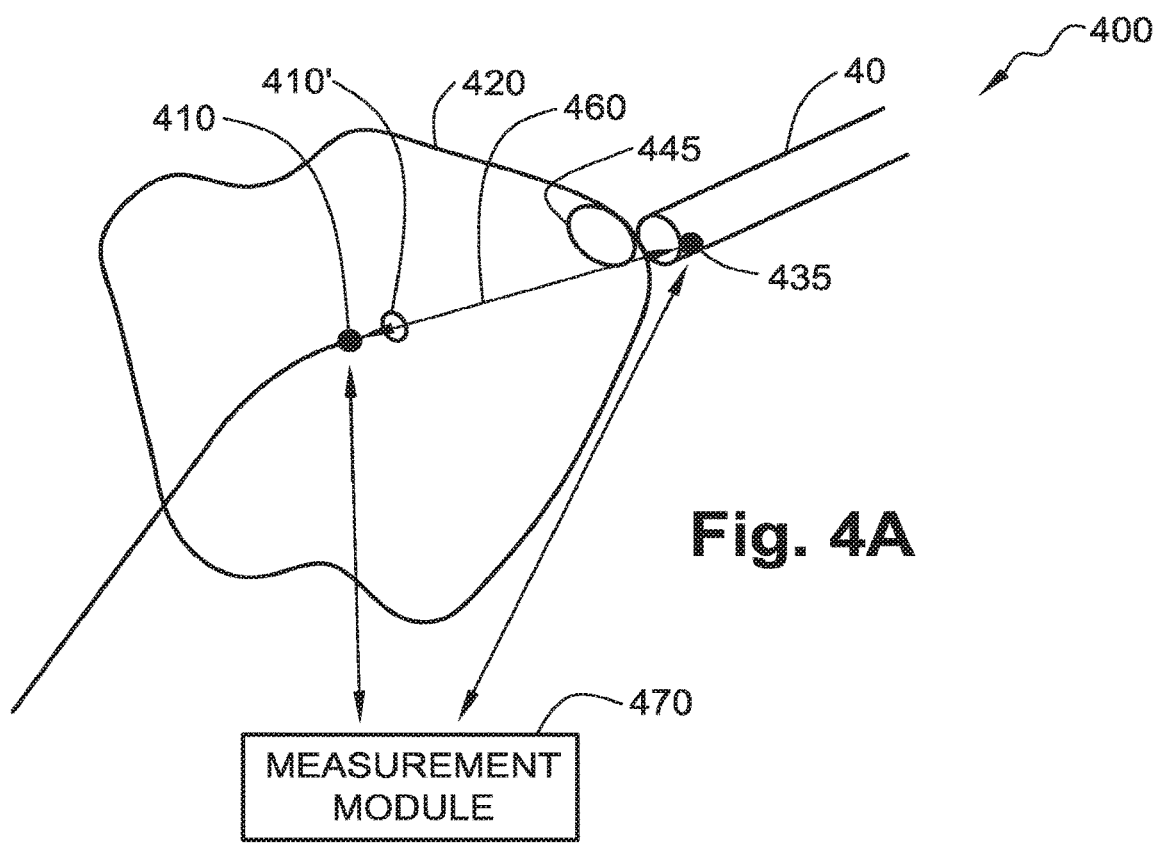
FIGS. 4A and 4B are side views of a substrate depicting an exemplary probe and an exemplary substrate position indicator according to an exemplary embodiment of the invention.
Figure 4B:
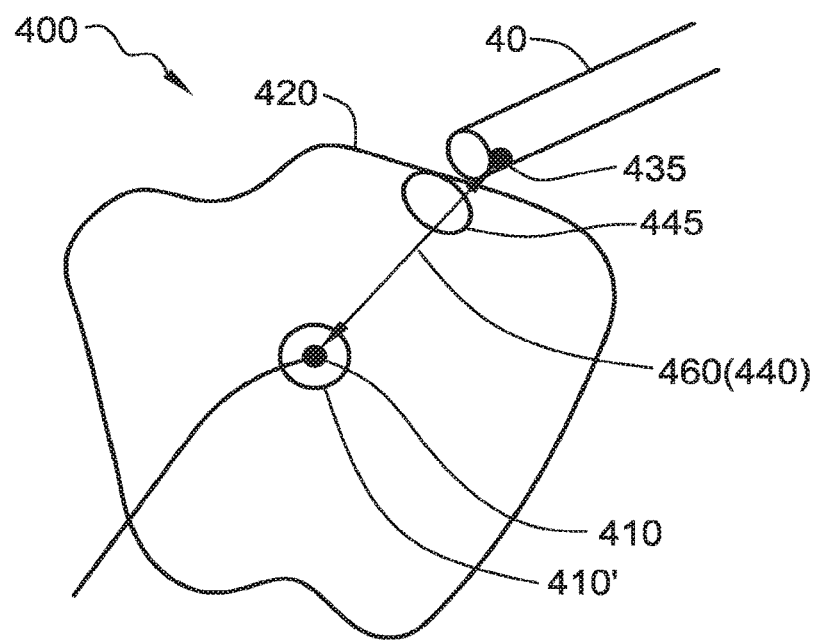

FIGS. 4A and 4B depict an exemplary measuring sub-system 400. Depicted exemplary measurement sub-system 400 employs a marker 410 in the substrate. Optionally, marker 410 has been implanted during a previous procure, such as image guided biopsy. Marker 410 can be passive or active.

Passive markers 410 can include, for example, a magnet or ultrasound reflector. Optionally, embodiments of the invention which include a passive marker 410 can include an active location detector 435 on probe 40 (e.g. a signal transducer).

Active markers 410 can include, for example, a radiofrequency RF or ultrasound (US) transducer. Optionally, embodiments of the invention which include an active marker 410 can include a passive marker 435 on probe 40.

In some exemplary embodiments of the invention, marker 410 is placed at or near a geometric center of substrate 420 (e.g. a tumor or excised tissue mass) indicated as 410'. It is often convenient to define 410' as an origin (0, 0, 0) for a three dimensional coordinate system defining locations on substrate 420.

In some exemplary embodiments of the invention (FIG. 4B), probe 40 includes an active sensor 435 adapted to measure a distance 460 and a direction, e.g. a relative vector (X,Y,Z) 440 between location 445 at which a substrate indicative datum is acquired and marker 410.

FIG. 4A depicts another embodiment of the invention in which positions of marker 410 in substrate 420 and marker 435 on probe 40 are each determined by a measurement module which determines a distance and direction 460 between measurement location 445 and center 410'.

According to one embodiment of the present invention, the probe 40 may include a structure, configured for receiving and holding a tissue specimen, wherein the tissue specimen includes tissue positional references and positional references, associated with the structure, for fixing the orientation of the tissue specimen, when held by the probe, so as to reflect the tissue specimen positional references. Such structure may be similar to various embodiments described, for example, in international publication number WO 2006/092797, entitled "Device And Method For Transporting And Handling Tissue", assigned to the common assignee of the present application and hereby incorporated by reference.

In some exemplary embodiments of the invention, system 100 includes a substrate position indicator 410 positioned at substrate 420 and a probe 40 operable to evaluate substrate status and output status indicative datum at individual points (e.g. 445) and measurement module 470 configured to determine a relative position of position indicator 410 and probe 40. In some exemplary embodiments of the invention, a controller (e.g. controller 22) coordinates operation of probe 40 and measurement module 470 so that said relative position is determined for each of said individual points. Optionally, a decrease in time difference between measurement of substrate status and of probe position contributes to an increase in accuracy of determined position for each substrate status measurement.

Optionally, the signal originates from probe 40 (e.g. from sensor 435) and is received at position indicator 410.

Optionally, the signal originates from position indicator 410 and is received at probe 40 (e.g. at sensor 435).

In some exemplary embodiments of the invention, measurement module 470 includes a position sensor adapted to determine a first position 445 of probe 40 (using marker 435) and a second position 410' indicating substrate location (using marker 410 to indicate (0,0,0)). According to these embodiments of the invention, measurement module 470 determines a relative position of marker 410 and marker 435 by comparing said first and second positions.

Other exemplary embodiments rely on any other technologies for determining relative position known to those of ordinary skill in the art.

Optionally, Measurement module is located external with respect to a patient body and/or with respect to substrate 420.

In some exemplary embodiments of the invention, system 100 includes an imaging module adapted to produce an image depicting said probe and said position indicator and measurement module 470 determines a relative position of probe 40 and substrate center 410' relative to image data. Optionally, the image data indicates markers 410 and/or 435.

In some embodiments of the invention, data indicative of substrate status is presented registered on a three dimensional representation of the substrate generated from the image data.

Optionally, probe 40 comprises a cutting tool. In some exemplary embodiments of the invention, the cutting tool is mounted at or near operative portion 42 and/or sensor 435 so that position and/or substrate status information for location 445 is relevant to the cutting tool.

In some exemplary embodiments of the invention, output module 1440 outputs relative position of probe 40 together with status indicative datum for each of individual points 445. Optionally, this contributes to an ability of registration module 1460 to register individual points 445 and/or grouped data 1450 on substrate model 1452.

Optionally, system 100 includes a procedure planning module 1480. Optionally, Procedure planning module 1480 is adapted to analyze said output from said output module and/or registration module 1460 and calculate a path. The calculated path optionally serves as a cutting path and/or a guide for delivery of implantable devices and/or medications. Exemplary implantable devices include, but are not limited to brachytherapy seeds and stents. Optionally, the path includes one or more location designations for performance of procedures (e.g. cutting and/or implantation, injection of medicine and/or ablation).

During the procedure planning (and/or guiding) actions other than cutting (e.g. navigation in consideration of anatomic features and/or administration of medication and/or implantation of devices) are optionally considered.

In some exemplary embodiments of the invention, planning module 1480 considers registration of status indicative data at multiple points 445 on substrate 420 registered to medical image data of any type when calculating a path. Alternatively or additionally, planning module 1480 is adapted to accept additional user input 1482 pertaining to a planned path (e.g. a cutting path) based upon output of said registration module. In some embodiments of the invention procedure planning module 1480 considers grouped data 1450 as well as outputs from output module 1440 and/or registration module 1460 inputs and outputs.

In some exemplary embodiments of the invention, planning module 1480 receives inputs from the user via an additional GUI. Optionally, the additional GUI includes a three dimensional graphical interface.

In some exemplary embodiments of the invention, planning module 1480 outputs a proposed path or other plan related information graphically, optionally as a three dimensional model. Optionally, graphic output of the proposed path or other plan related information is presented overlaid and/or registered with a medical image.

Exemplary Adaptation for Surgical Supervision

Figure 16:
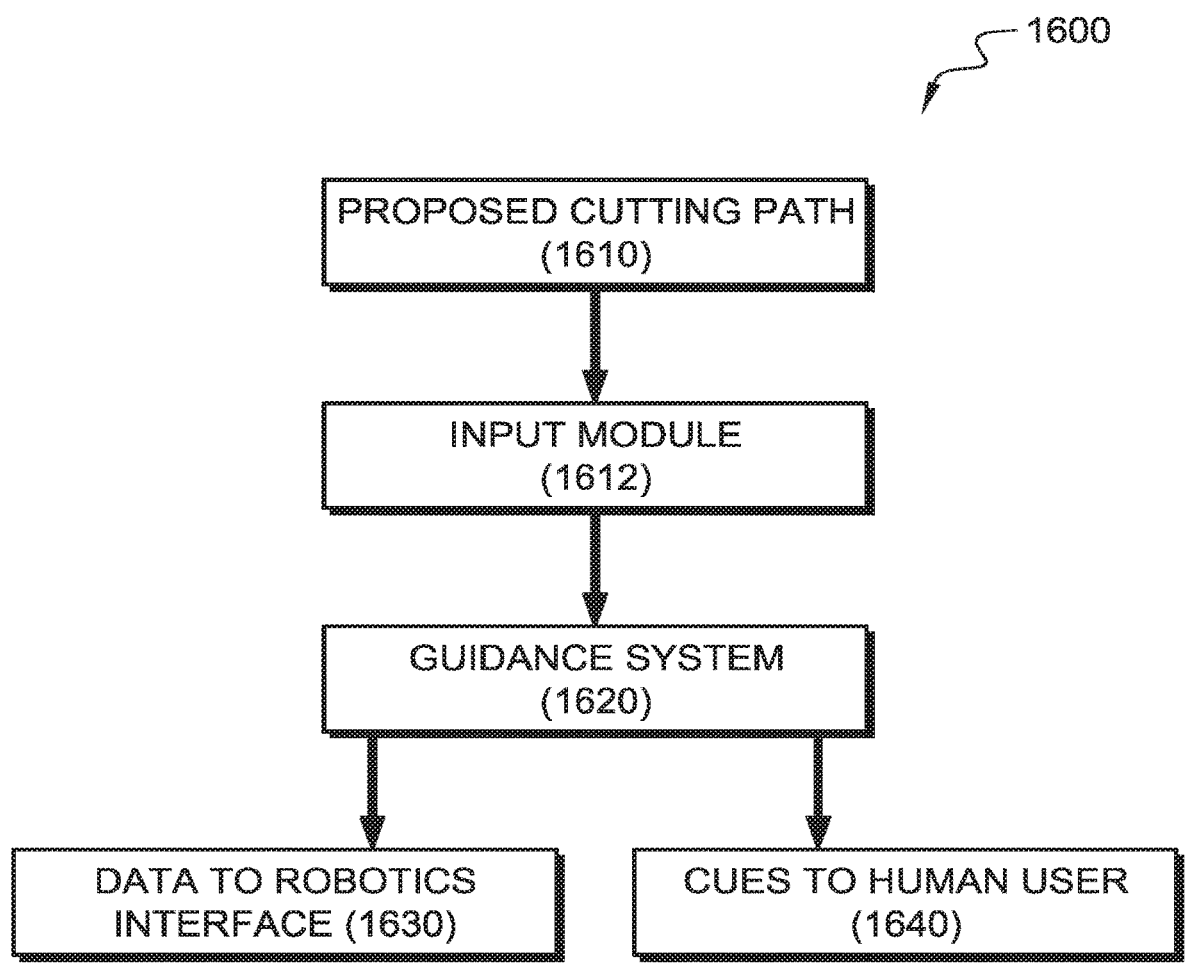
FIG. 16 is a schematic representation of an exemplary supervision system according to some embodiments of the invention.

FIG. 16 depicts a surgical supervision system 1600. Optionally, system 1600 aids in performance of surgery.

Depicted exemplary system 1600 includes an input module 1612 adapted to receive a proposed path (e.g. cutting) 1610 from a procedure planning module. The procedure planning module is optionally a planning module 1480 as described above. Depicted exemplary system 1600 also includes a guidance system 1620 adapted to output guidance instructions to guide a surgical tool along said path. Optionally, the instructions are provided in a data format 1630 suitable for use by a robotic interface and/or as cues 1640 suitable for use by a human user.

For example, display 300 (FIG. 3A) can include an image overlay such as probe reading (e.g. a binary reading per point) with a window showing an image such as a 3D image of the substrate and/or a characterized an anatomic feature. The reading optionally enables guiding of and/or instructions for guiding a surgical tool to a specific region shown on display 300. Optionally, probe readings are registered on the image.

Figure 17:
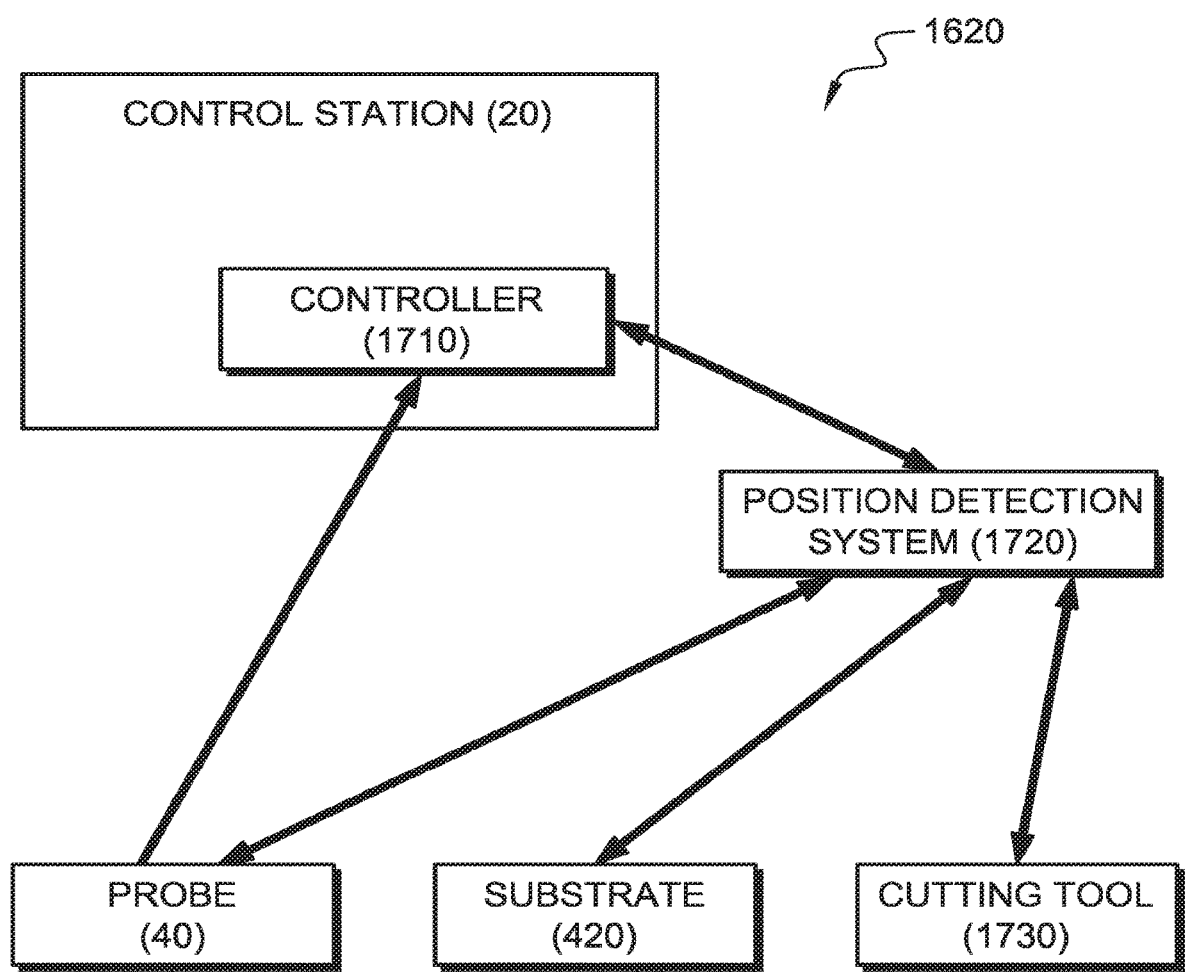
FIG. 17 is a schematic representation of one possible exemplary guidance system of FIG. 16 in greater detail.

FIG. 17 is a schematic representation of one possible configuration of a guidance system 1620 as shown in FIG. 16 in greater detail. In the depicted exemplary configuration, position detection system 1720 determines positions of substrate 420 and probe 40 using any technology known in the art. Depending upon actual implementation, position detection system 1720 may rely upon markers implanted in substrate 420 and/or installed on probe 40 as described hereinabove.

In some exemplary embodiments of the invention a cutting tool 1730 is provided as a separate unit from probe 40. According to these exemplary embodiments, position detection system separately determines a position of cutting tool 1730.

In other exemplary embodiments of the invention cutting tool 1730 is provided as part of probe 40. According to these exemplary embodiments, position detection system concurrently determines the position of cutting tool and of probe 40.

In the depicted exemplary configuration, position detection system 1720 is in communication with a controller 1710, optionally integrated in control station 20.

In some exemplary embodiments of the invention, position detection system 1720 determines a relative position of probe 40 and/or cutting tool 1730 with respect to substrate 420.

In other exemplary embodiments of the invention, controller 1710 determines a relative position of probe 40 and/or cutting tool 1730 with respect to substrate 420 based upon position data received from position detection system 1720.

In the depicted exemplary configuration, controller 1710 also receives data indicative of substrate status as described hereinabove from probe 40. In some exemplary embodiments of the invention, controller 1710 integrates and/or correlates this data with corresponding position data for probe 40 to produce position correlated substrate status data. Optionally, controller 1710 constructs a status map from the position correlated substrate status data.

In some exemplary embodiments of the invention, controller 1710 compares the status map to the proposed path provided by input module 1612 (FIG. 16). As probe 40 and/or cutting tool 1730 are moved, the status map and/or proposed path can be updated by controller 1710 to produce a current status map and/or a current path.

In some exemplary embodiments of the invention, controller 1710 formulates data 1630 for the robotic interface and/or cues 1640 for the human user based upon the current status map and/or the current path.

Exemplary Probe Unit

Referring again to FIG. 1, exemplary embodiments of the invention reside in substrate probe 40. Optionally, probe 40 is adapted to interact with system 100.

Depicted exemplary substrate probe 40 includes a data acquisition module adapted to engage a substrate at a user selected point, analyze the substrate and produce a datum indicative of substrate status at said point. The data acquisition module is depicted schematically as operative portion 42.

In some exemplary embodiments of the invention, operative portion 42 includes a pair of electrodes in communication with a cavity and a vacuum source configured to draw a portion of a substrate into the cavity so that it contacts the electrodes.

Depicted exemplary substrate probe 40 includes a user input device in the form of buttons 43 (three are depicted). In some exemplary embodiments of the invention, the user input device is configured to group individual datum into groups of data.

Optionally, fewer or more than three buttons 43 are provided. In some exemplary embodiments of the invention, a single button serves as a user input device. Optionally, buttons 43 are replaced by other mechanical, electronic or electromechanical input hardware (e.g. slider, rheostat, scroll wheel, microswitch).

Depicted exemplary substrate probe 40 includes a signal conduit 5 adapted to relay electrical and/or optical signals and a lumen adapted to relay a negative pressure from an external vacuum source to the data acquisition module (e.g. operative portion 42). In some exemplary embodiments of the invention, the lumen adapted to relay negative pressure resides in conduit 5. In other exemplary embodiments of the invention, the lumen adapted to relay negative pressure is provided separately.

Depicted exemplary substrate probe 40 includes a connector to an external data analysis component. Optionally, this connector resides in conduit 5 and/or relies upon a wireless link.

In some exemplary embodiments of the invention, probe 40 is provided as a sterile medical device. Optionally, probe 40 is provided in packaging configured to insure sterility until probe 40 is opened in an operating theater. Considerations in sterile packaging configuration are known to those of ordinary skill in the art of medical diagnostics and will be easily applied to embodiments of the invention.

In some exemplary embodiments of the invention, probe 40 comprises a user perceptible indicator. Optionally, the indicator provides a visible and/or audible indication as described above.

In order to make apparent some advantages of probe 40, an exemplary use scenario is described in detail.

Figure 5:
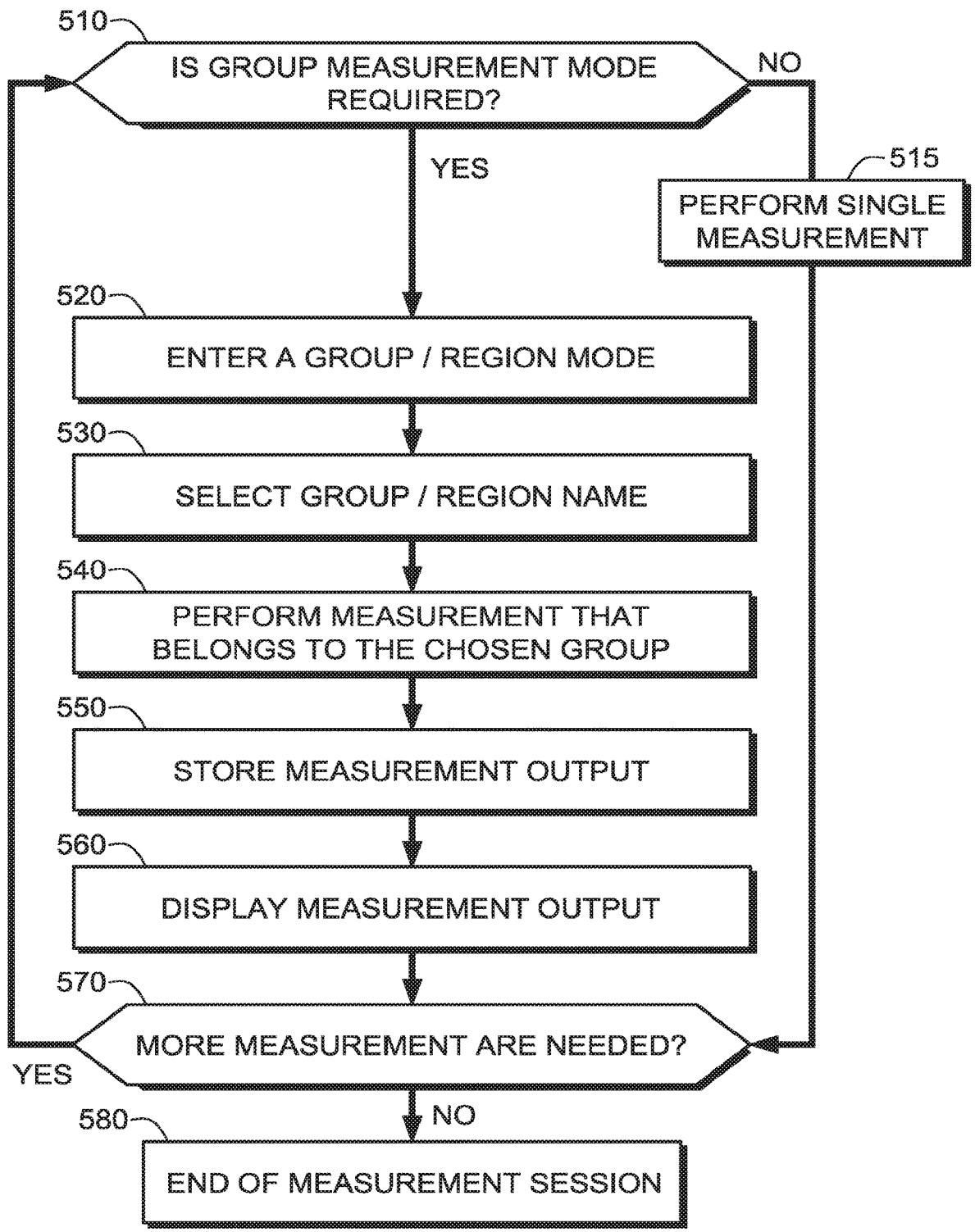
FIG. 5 is a simplified flow diagram of a method according to one exemplary embodiment of the invention.

FIG. 5 is an exemplary simplified schematic flow-chart of a method 500 for measuring and displaying Measurements outputs of a substrate. At 510 a determination of whether group measurement mode is required is made.

If no, then at 515 a single measurement is performed, for example by probe 40.

If yes, then at 520 a group mode is entered and a group/region name is entered or selected from a predefined list at 530. Entry can optionally be by a user (e.g. physician) or automatic as described hereinbelow in relation to FIG. 6.

At 540 one or more measurements which belong to the chosen group are performed, for example by probe 40.

At 550 measurement outputs are stored. Storage can be, for example in control station 20 or in database storage unit 48 of probe 40.

At 560 measurement outputs are displayed. Display is optionally on display screen 24 or indicator 1.

At 570 a determination of whether more measurements are necessary is made.

If yes, return to 510 with probe 40 being moved to a new point and/or substrate region.

If no, end measurement session at 580.

Exemplary Data Entry Interface

Figure 6:
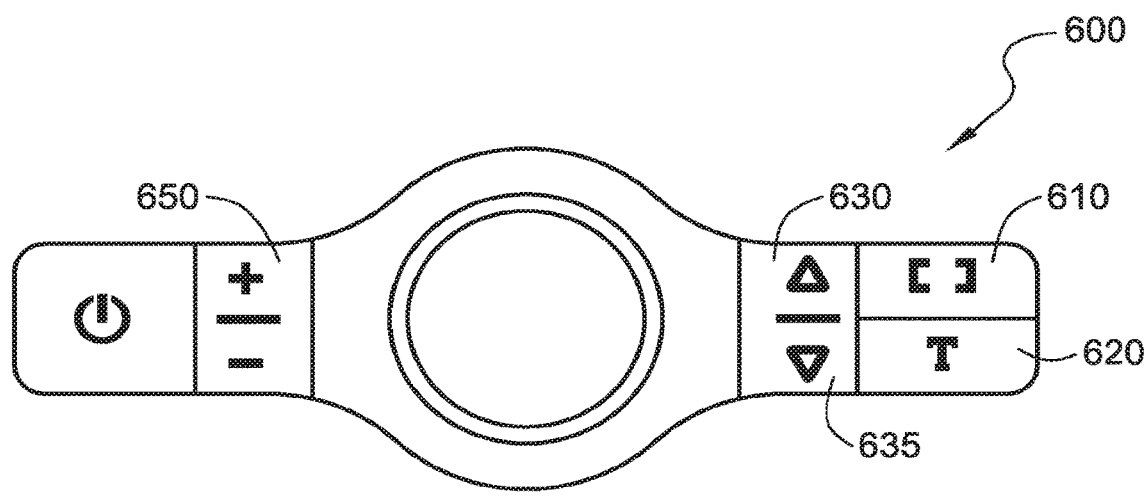
FIG. 6 is a schematic of an exemplary user input interface according to one embodiment of the invention.

FIG. 6 is schematic diagram of an exemplary embodiment of front panel buttons 600 of console 20.

According to some embodiments of the invention, operations done using the console front panel buttons 600 may alternatively be performed using button(s) 43 of probe 40.

For example, a double click on button 43 may initiate group mode process. Optionally, a consecutive number, starting for example with '1', is automatically presented in response to the double click. Alternatively, letter can be employed in a predefined order, for example according to M/L/D/SF/I/S convention.

Figure 12:
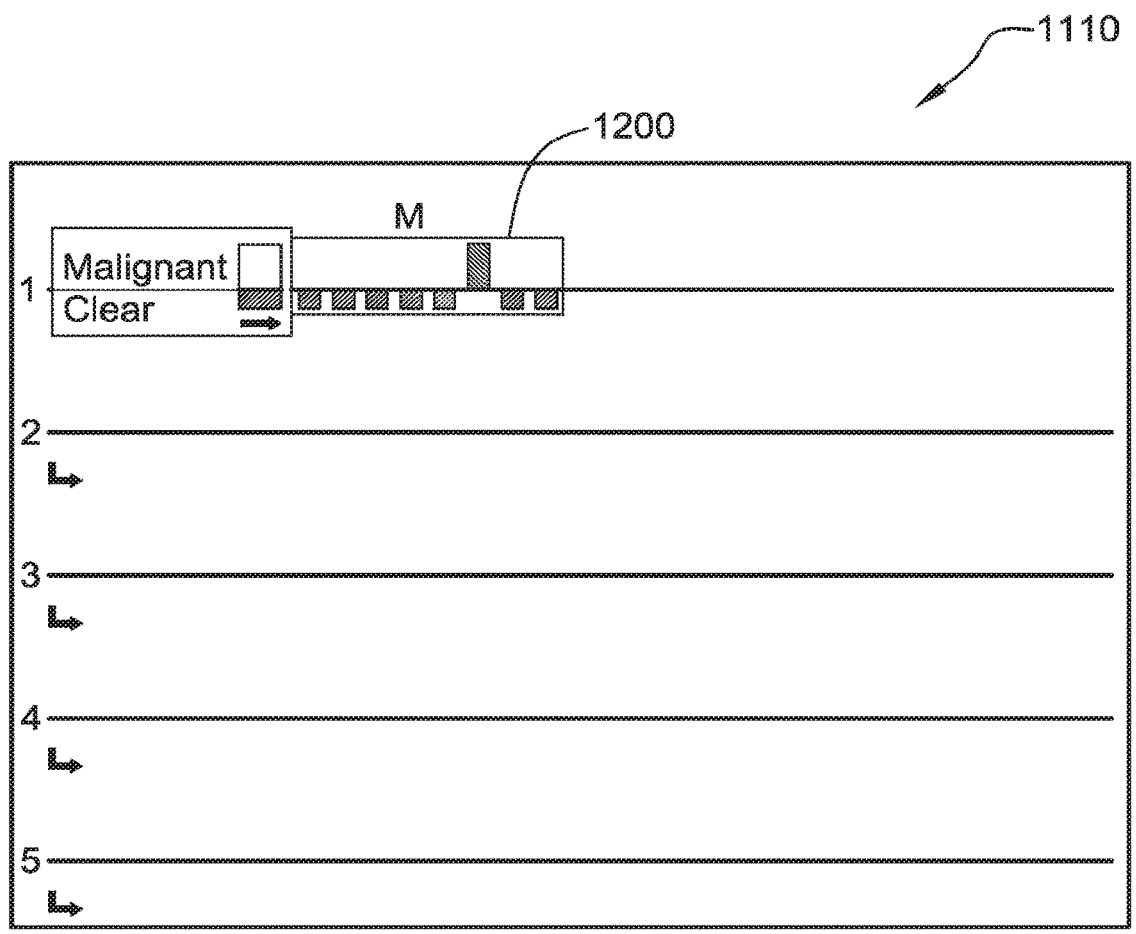

FIG. 12 depicts an exemplary display screen 1110 in which a second double click optionally closes a group mode, for example depicted first group 1200 (M). Optionally, closing of a group closes a frame around the group as shown.

Figure 13:
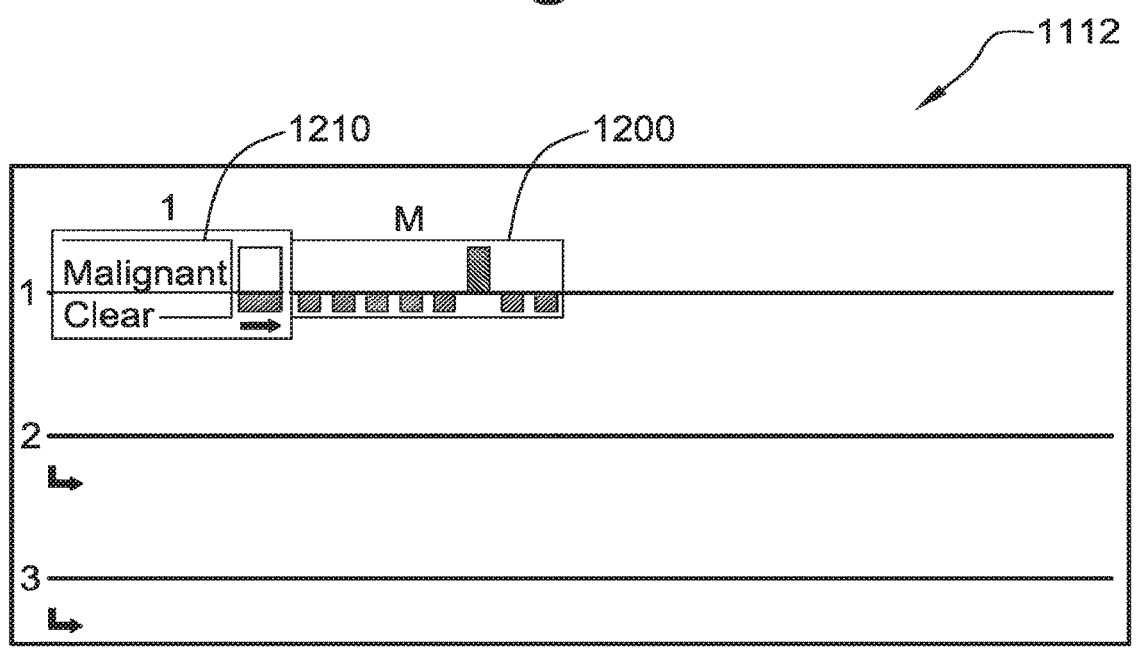

FIG. 13 depicts an exemplary display screen 1112 in which an additional double click opens a second group 1210 (1) as shown. Optionally, opening of a group causes a new frame to appear. Optionally the new frame is open on its left side as depicted.

Alternatively, button 610 on panel 600 (e.g. of console 20) can be operated in an analogous manner to perform the same functions.

Figure 9:
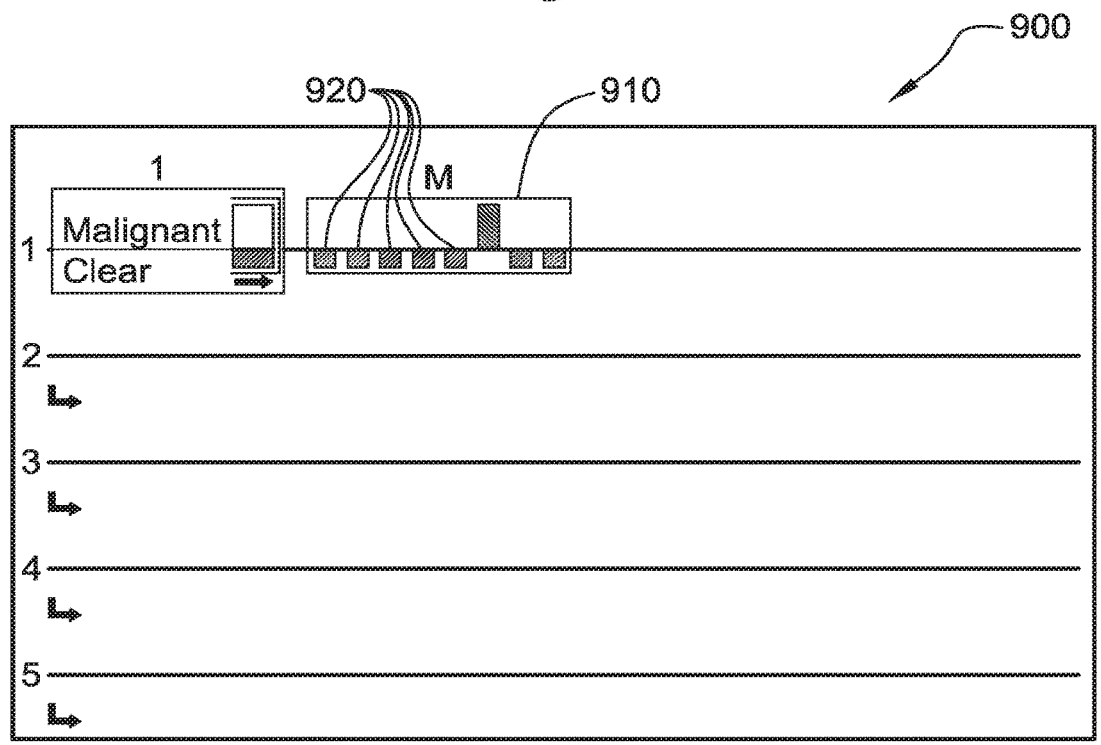

FIG. 9 depicts an exemplary display screen 900 in which a "closed" group 910 (optionally representative of a region [e.g. M] on the substrate) including one or more measurements outputs 920 is illustrated. According to some embodiments of the present invention, a measurement may also be initiated immediately, without entering a group mode. A long single press on the button 43 of probe 40 or button 620 on console 600 enters a group name mode. Optionally, a menu of names is accessed (e.g. Medial—M, Lateral—L, Posterior (Deep)—D, Anterior (Superficial)—SF, Inferior—I, Superior—S, #—number that was automatically chosen for the group, CAV—to enter into relevant sides of the cavity).

In some embodiments each short press on probe 40 button 43 or alternatively, by pressing on either button 630 or button 635 on console front panel 600 presents a different group name, for example in cyclic consecutive order.

Figure 11:
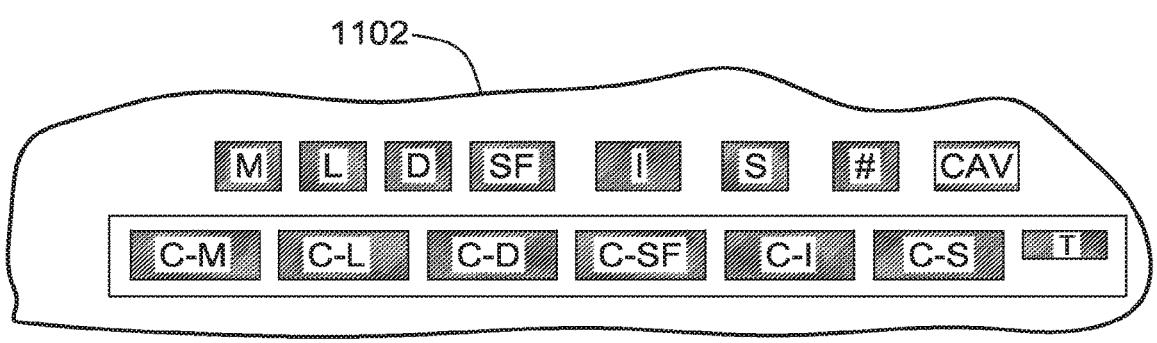
FIG. 11 is an exemplary set of user inputs devices according to one embodiment of the invention.

FIG. 11 depicts an exemplary set of user inputs (e.g. buttons) 1102. According to some embodiments of the invention buttons 1102 may be provided in the control station 20 or probe 40. Optionally, buttons are labeled with group names corresponding to region names as indicated. Alternatively or additionally, a similar set of names can be presented as a menu on a display screen.

According to some embodiments of the present invention, the group to be presented after a first press will be the next group that follows after the previous chosen group. A sign '#' may represent a group number which was automatically chosen by the system. Once the region or group name is approved (e.g. by a long press on button 43 or 620), the user may scroll between a list of regions (e.g. using button 650). A long press on button 43 or 620 approves a specific region as indicated by group name. In case one of the region options was chosen, entering group name mode for next group will start immediately with a list of regions options. A group's name may be approved by a long press on probe's button 43 or by pressing on button 620 on console's front panel 600.

Figure 10:
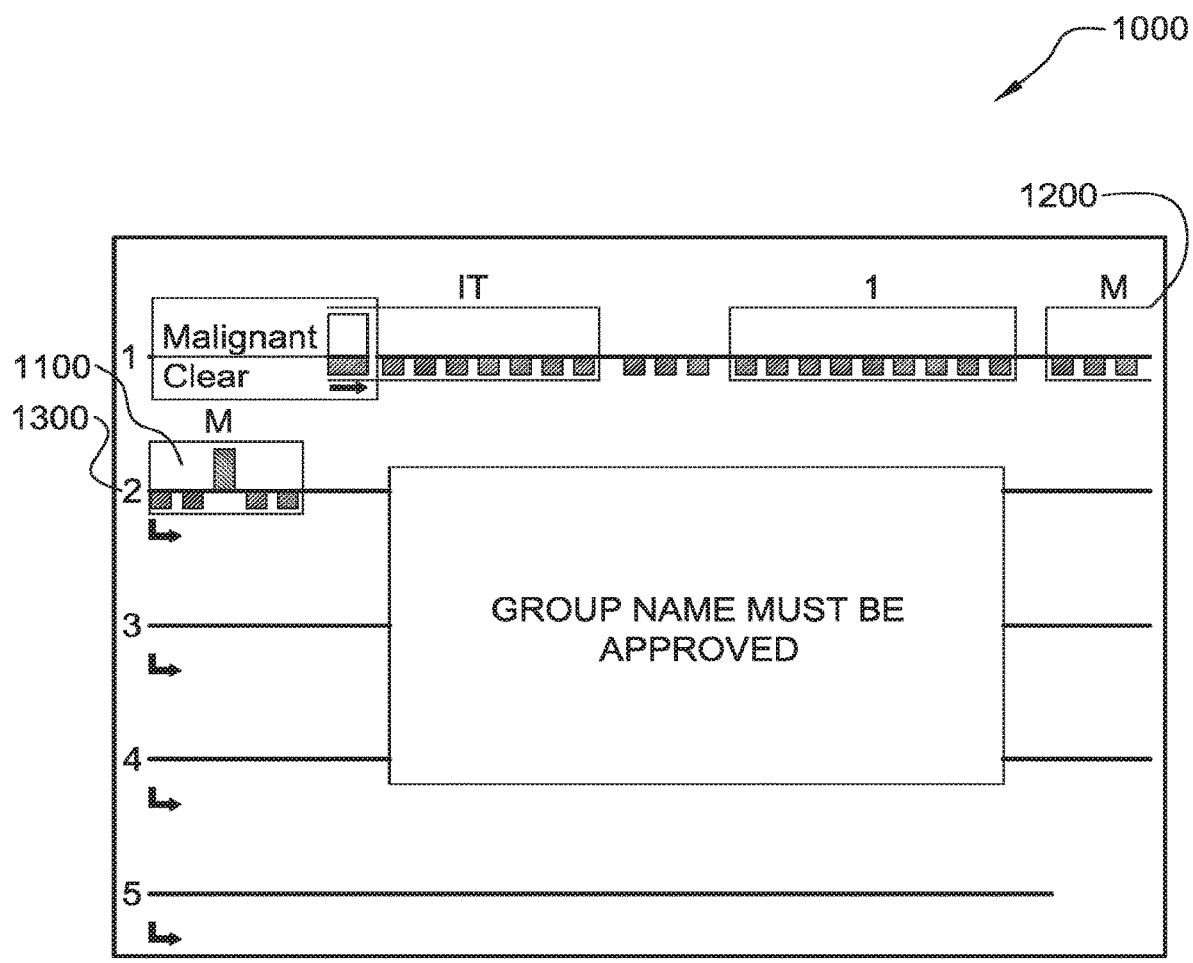

FIG. 10 depicts an exemplary display screen 1000 According to some embodiments of the present invention, a group name may be colored, for example in red until it is approved by long button press on button 43 or 620. Once approved, the color of the group's name may be switched for example to yellow. In some embodiments measurements can not be taken until group is approved. Optionally, a group name may be changed, even after it was approved, as long as the group was not closed. In some embodiments after a group was closed, the group name can not be changed. In some embodiments, actions can not be done before approving a group name. For example a message, such as an audio or digital message, will pop up on the screen in cases such as: group name was not approved, and/or after two seconds from choosing a name.

To exit group mode a user may double press on button 43 or 610 on the console. Optionally, the user may open a second group by double clicking button 43. According to some embodiments, the measurements can be performed immediately without choosing group name. In case a group name was not chosen it could be chosen at any time, for example as long as the group mode is active. In some embodiments a group name may be chosen more than one time.

Figure 8:
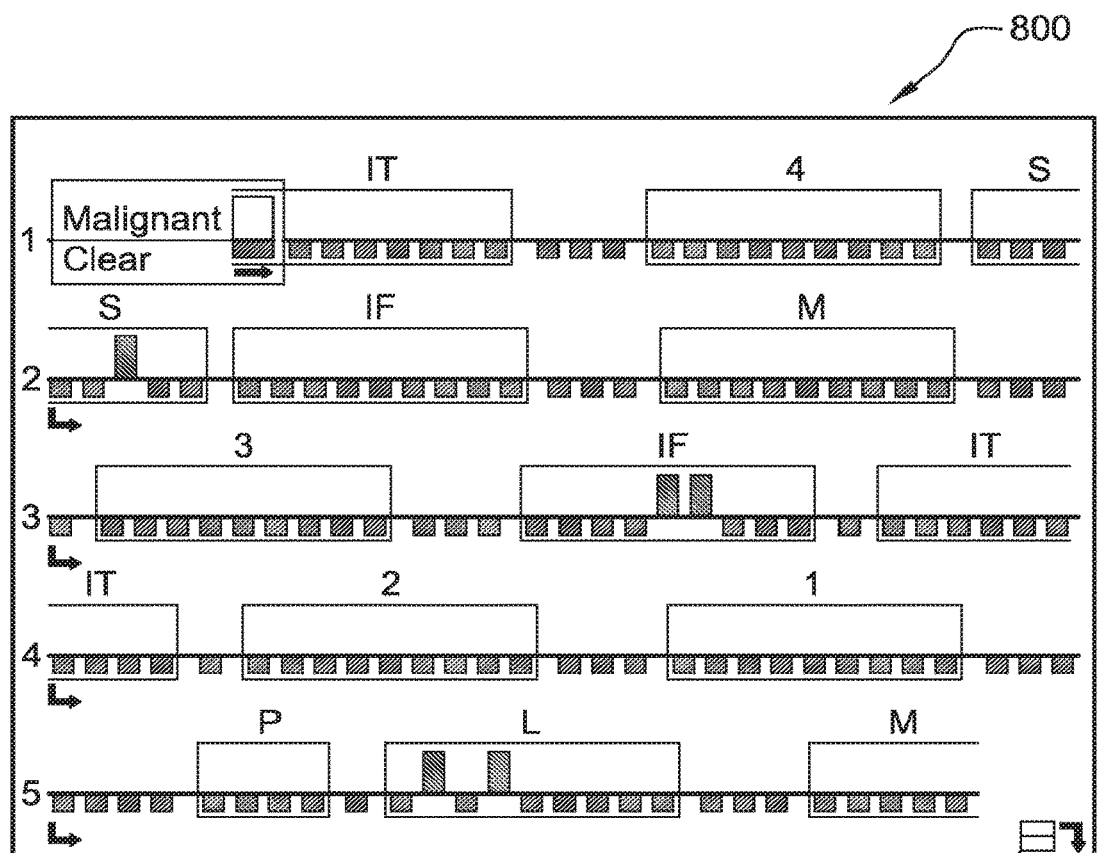

FIG. 8 illustrates an exemplary embodiment of a display screen 800 in which a output of a next measurement "pushes" previous measurements to a next row which is not visible on the screen, and a scroll indicator 810 is activated, as shown in FIG. 8. The user may use button 43 or button 640 or the joystick for scrolling up or down the measurements.

According to some embodiments of the present invention, when a screen line or row is full with measurements outputs or region output the "next" measurement output of the same region output or the next single measurement output may be presented in the "next" row. For example, as shown in FIG. 10, the next measurement output 1100 of region output 1200 is displayed in the next row 1300.

An error massage may be displayed on probe 40 or on display screen 24. In some embodiments an indication of an error message may be activated using for example an audio indicator machine.

A group may be selected before the measurements related to that group have been initiated. Alternatively, the group may be selected after some of the measurements which related to the group have been acquired or alternatively the group may be selected after all the measurements related to the group have been acquired.

Figure 7:
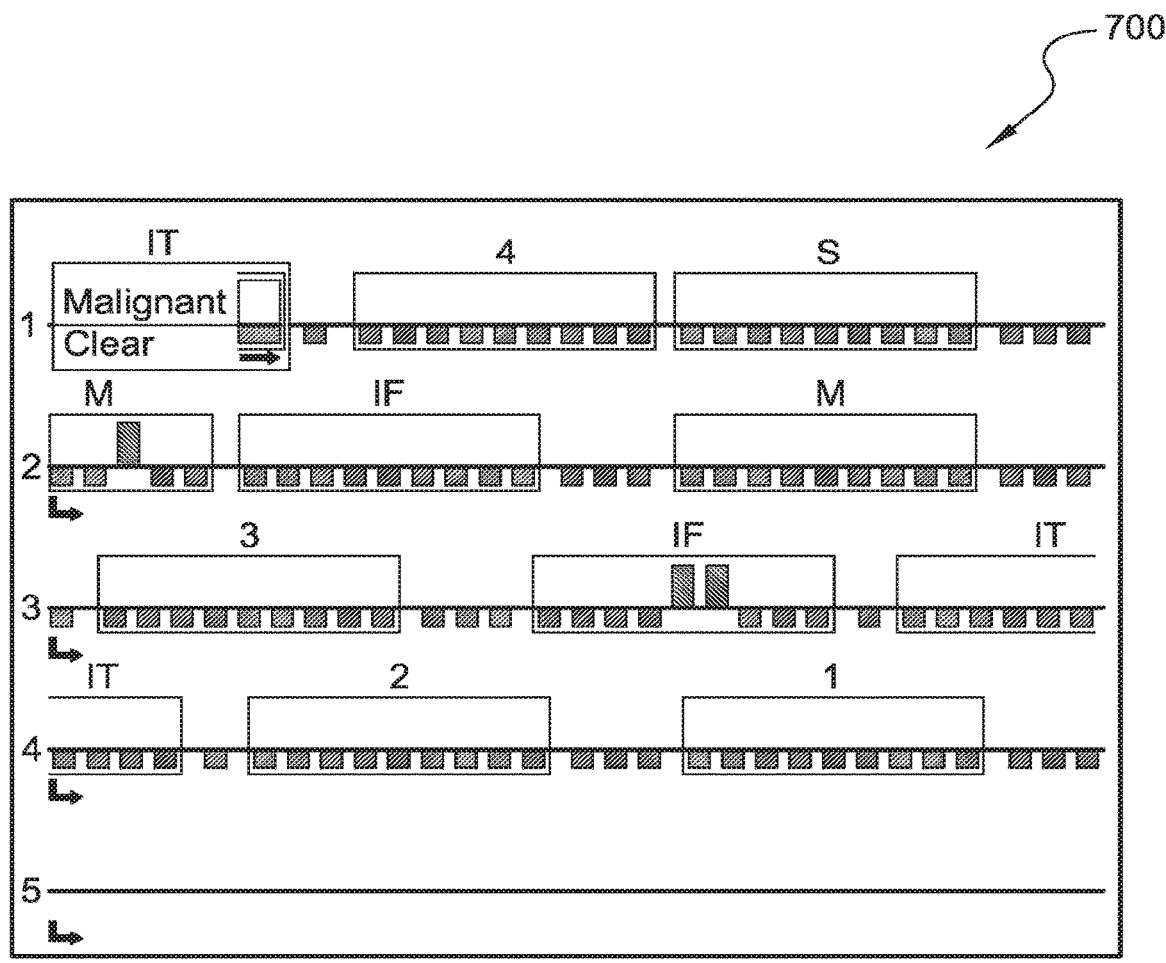
FIGS. 7 to 10, 12 and 13 are schematic of exemplary information screens according to embodiments of the invention.

FIG. 7 depicts an exemplary output screen 700 in which current measurements are highlighted. Highlighting can be, for example, by changing characteristics of background and/or a frame indicating a current group and/or characteristics of a current measurement (e.g. bar width or color).

According to some embodiments of the present invention, data from a session is saved in storage unit 48 for further analysis. Optionally, session data may also be exported and transmitted to an external device/computer or to an external memory device such as a removable memory e.g. a Diskon-Key or other small and portable memory device. Session data recorded or saved may be used, for example, in additional procedures, such as pathology procedures, related to the examined tissue. Session data which was recorded or saved may be also used in additional procedures, such as additional surgical or diagnostic procedures on a same subject.

Exemplary Analysis with Registration

Referring again to FIG. 14, additional exemplary embodiments of the invention which are independent of data grouping are described.

Some exemplary embodiments of the invention are of an apparatus 1400 for analysis of a substrate including a probe 40 as described hereinabove, a modeling module 1454 adapted to produce a three dimensional model of the substrate and a registration module 1460 adapted to indicate the specified locations on the model. Optionally, the modeling module relies upon defined position coordinates 1422 and/or substrate models 1452 (e.g. predefined geometric models or realistic modes indicative of actual substrate shape or models based on medical image data).

Optionally, the apparatus includes an output module adapted to present an indication of substrate status at each of the specified locations on the model. In some exemplary embodiments of the invention, presentation is as an overlay. In some exemplary embodiments of the invention, the model is a 3D model which can be manipulated (e.g. rotated or inverted) during viewing.

In some exemplary embodiments, apparatus 1400 is adapted to accept a user input specifying a position of said locations (e.g. user provides coordinates 1422).

In other exemplary embodiments, apparatus 1400 is adapted to determine a position of said locations. Optionally, apparatus 1400 employs position sensors 1420 adapted to determine a position of said locations.

Optionally, output of registered data from registration module 1460 is to one or more of a graphic display, a printer and a memory.

As indicated above, the apparatus of the present invention may be used for identification of a clean margin around a substrate (an abnormal tissue portion) which has been or is to be removed. In this connection, reference is made to FIGS. 18a-18c schematically illustrating the principles of providing a clean margin, in accordance with the present invention.

Figure 18B:
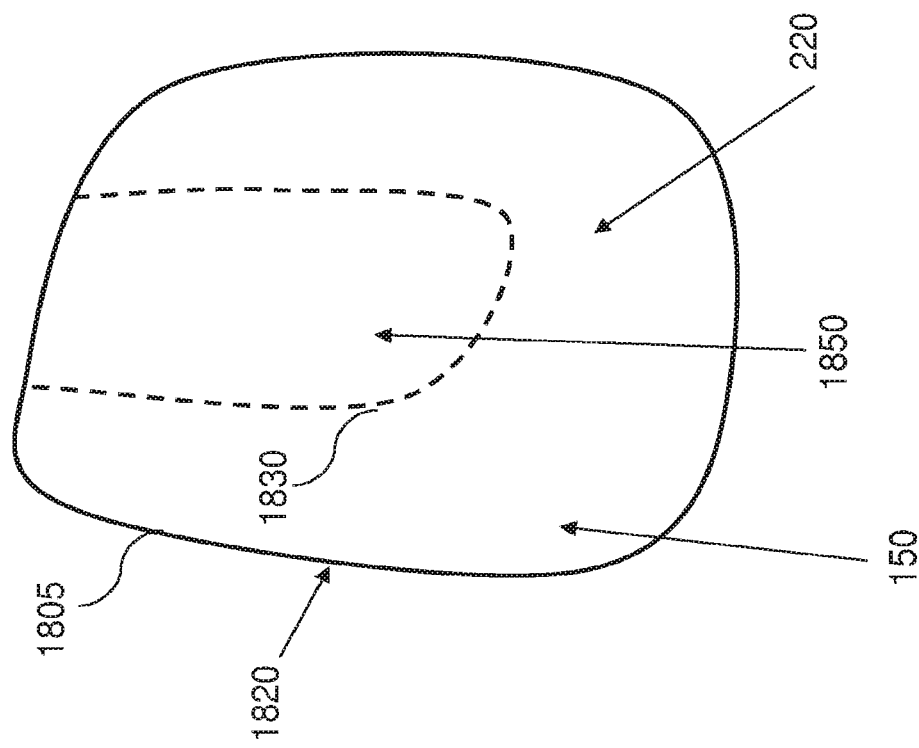
FIGS. 18A to 18C illustrate the principles of a clean margin technique in accordance with the present invention, where
Figure 18A:
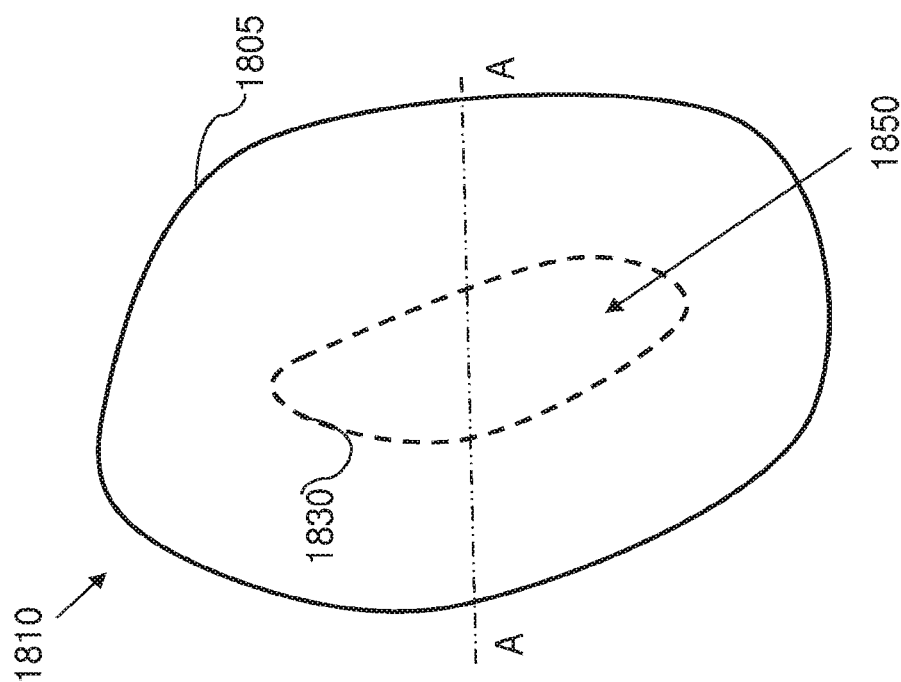

FIGS. 18A and 18B illustrate a top view 1810 and a cross sectional view 1820, respectively, of a tissue part 1805 and an incision surface contour 1830 within tissue part 1805. The incision surface 1830 surrounds a tissue region (portion) 1850 which may be removed from the tissue part 1805 during a surgical process for achieving a clean margin (i.e. obtaining the incision surface 1830 or the near zone at the incision surface 1830 with no abnormal tissue cells). In other words, identification of a clean margin within the surrounding or periphery of the tissue portion 1850, which has abnormal tissue cells signifies that tissue 1850 can be removed and no removal of additional surrounding tissues is required.

The tissue portion 1850 may include for example a lesion, or a tumor, or any other abnormal tissue. The lesion, or the tumor, or the abnormal tissue, is to be fully and completely removed, with a clean margin surrounding it. The tissue part 1805 and the tissue portion 1850 therein may be a skin portion, a body lumen portion, an organ, an anatomical feature, some portion of intra-corporeal tissue, or a combination theirs. The tissue 1850 may be removed from a body, either completely or partially. The incision surface 1830 may be an incision surface contouring an organ, or an anatomical feature. According to some embodiments of the present invention the incision surface 1830 may be defined by a diagnostic modality, or by a surgeon.

Figure 18C:
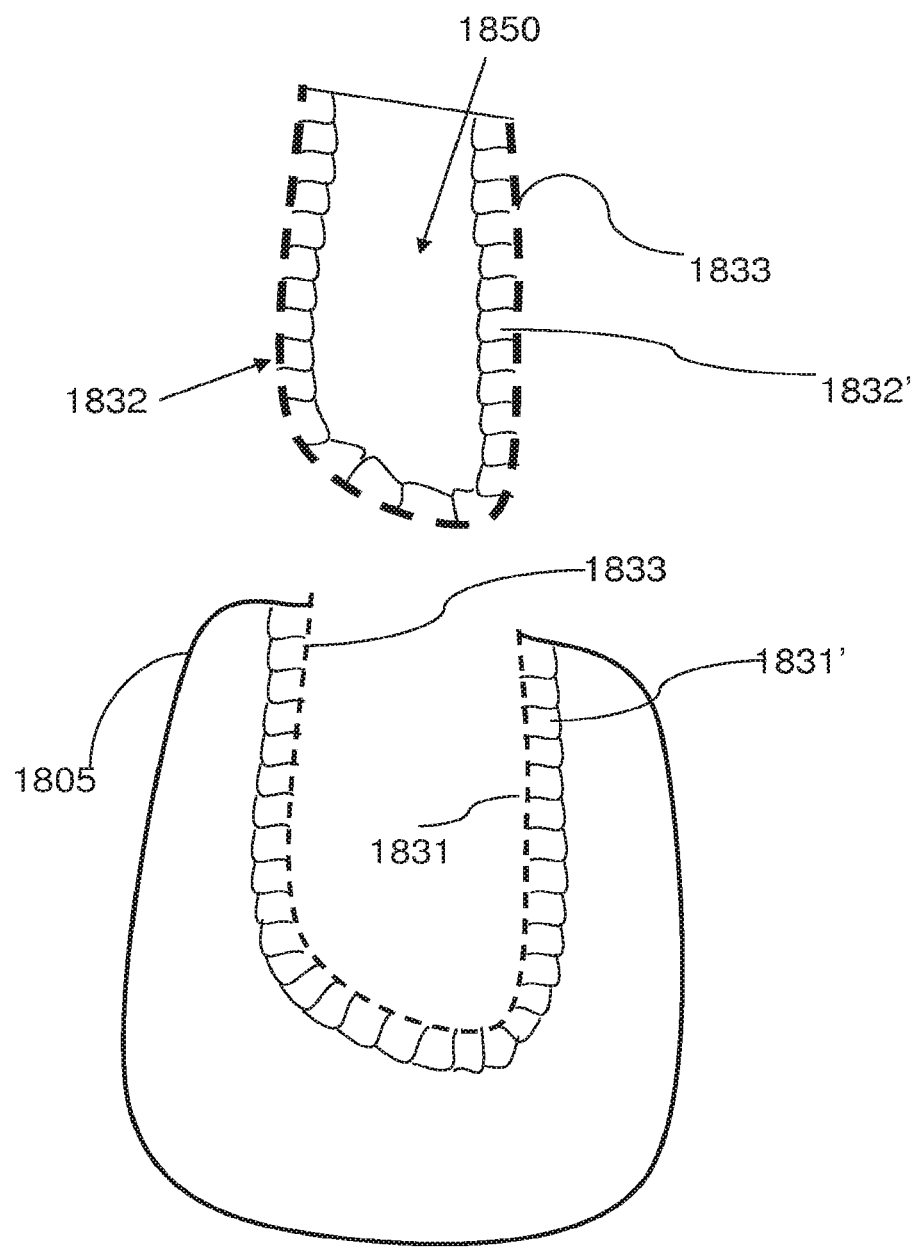

As shown in FIG. 18C, the excision of tissue portion 1850 from the tissue 1805 (along the incision contour 1830) forms two separated surfaces (illustrated by a dashed curve 1833). A first surface, e.g. surface 1831, includes newly exposed surface segments 1831' of the tissue 1805. The surface 1831 may include the inner surface, the intact tissue related surface, the cavity surface. A second surface, e.g. surface 1832, includes newly exposed surface segments 1832' of the tissue portion 1850. The surface 1832 may also be termed as the outer surface, the removed tissue related surface, the excised tissue related surface, the lump surface or the substrate surface.

A process for achieving a clean margin includes a characterization process followed by an incision/additional tissue removal process. According to some embodiments of the present invention, during the characterization process the inner surface 1831 and/or the outer surface 1832 are characterized to determine whether a tissue portion such as the tissue portion 1850 has been excised with the clean margins. The incision/additional tissue removal process follows the characterization process. The characterization and incision/additional tissue removal cycle may be continued until for example the characterized tissue surface contains no cancerous cells, and thus has a clean margin. Alternatively, the incision/additional tissue removal process following the characterization process may include removal for example of a specific organ, or anatomical feature, for example without additional characterization cycles. According to some embodiments of the present invention, during or following the incision/additional tissue removal process an additional characterization process and/or corrections for the clean margins may be preformed.

Figure 19A:
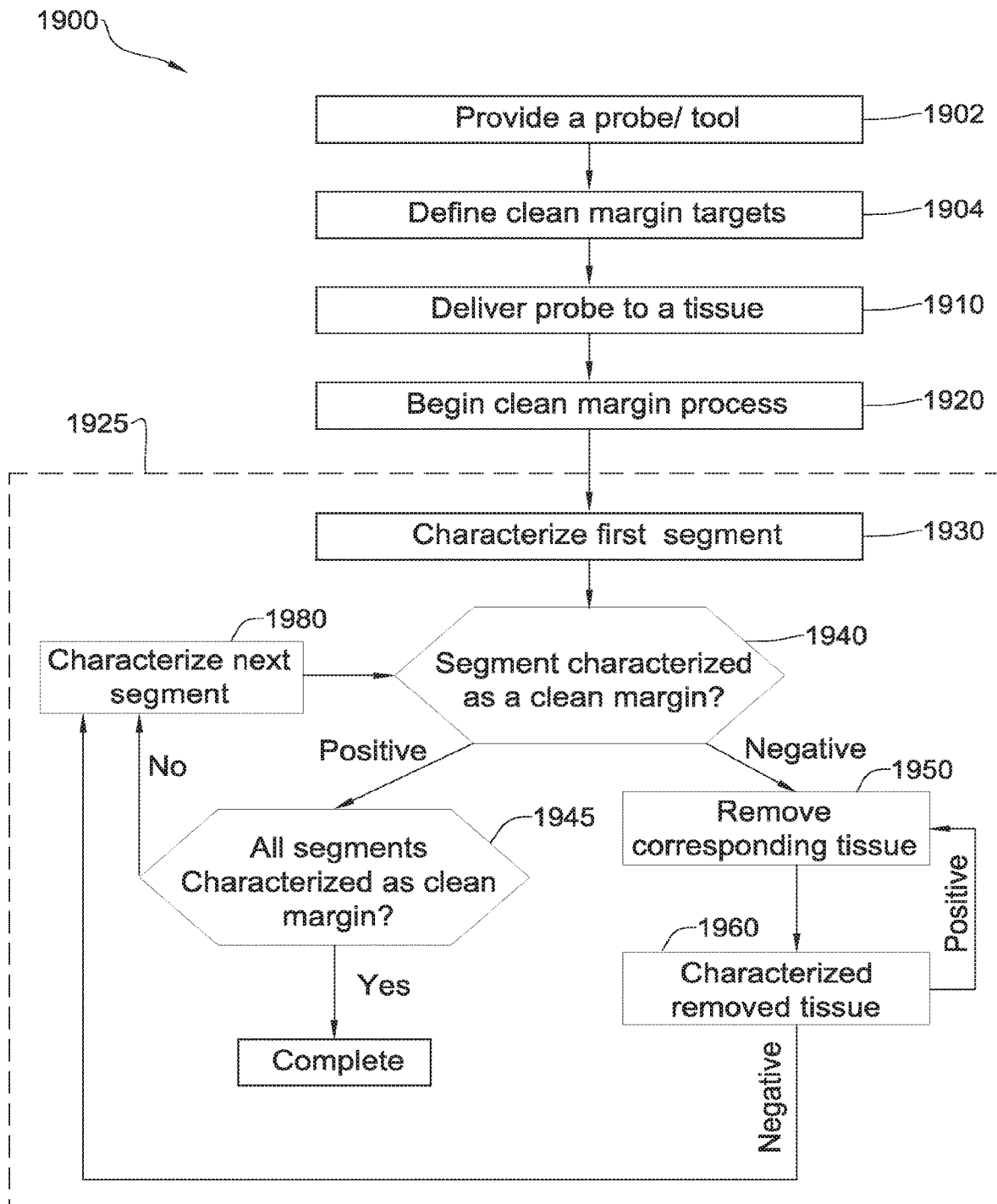
FIGS. 19A and 19B illustrate flowcharts of a method of the present invention for providing a clean margin of healthy tissue around a malignant tumor or abnormal tissue.
Figure 19B:
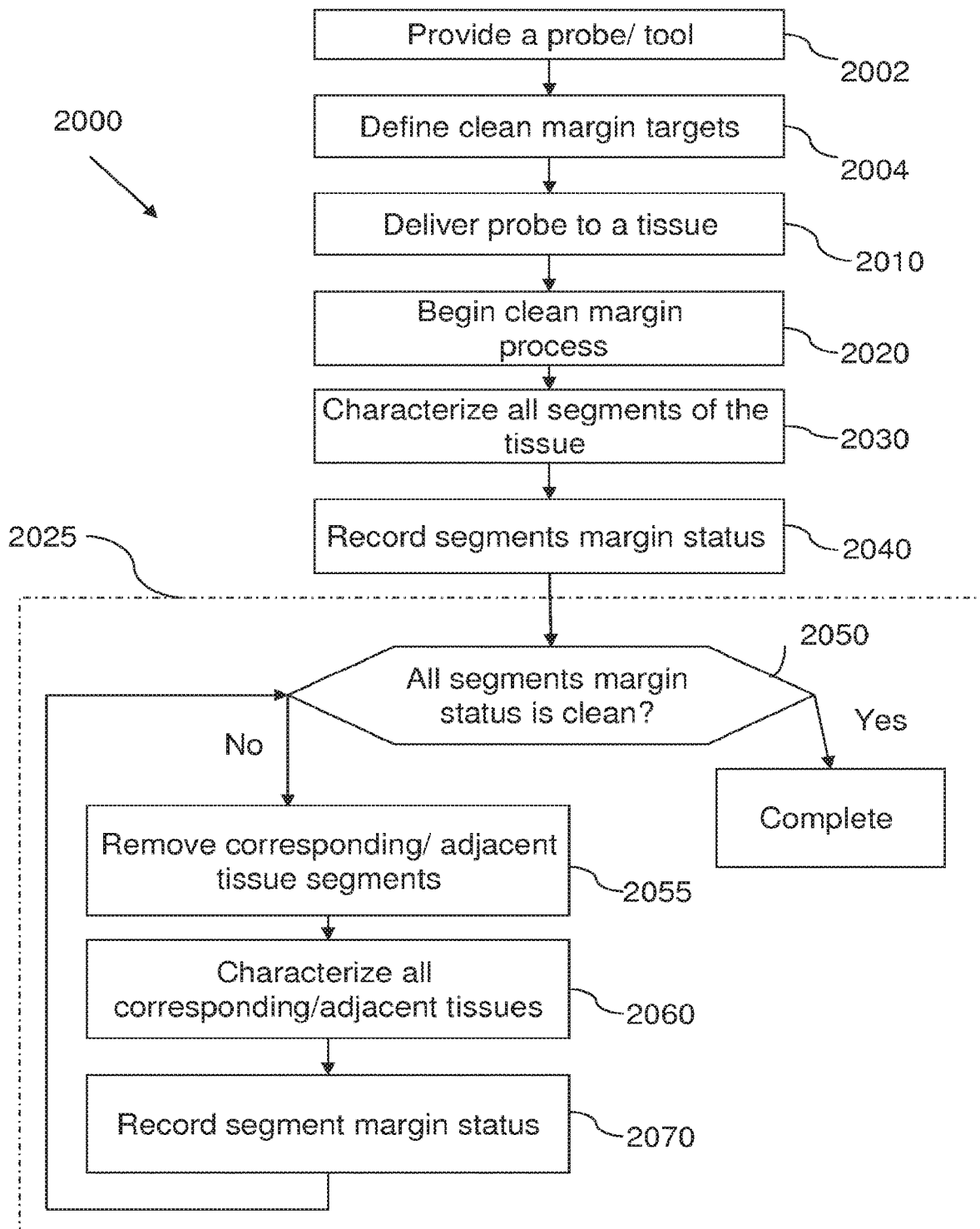

Reference is now made to FIGS. 19A and 19B illustrating flowcharts 1900 and 2000 of a method for providing a clean margin of healthy tissue around a malignant tumor or abnormal tissue, in accordance with some embodiments of the present invention. As illustrated in flowchart 1900, a medical probe or tool for characterizing a tissue is provided

1902. The probe includes one or more tissue-type sensors, or an array of sensors for determining the characteristics of a tissue surface, such as tissue surfaces 1831 or 1832, for example in the near zone volume of the tissue surface. According to some embodiments of the present invention, the probe is configured as the above-described probe 40 comprising a tool for clean-margin assessment. According to some other embodiments of the present invention, the probe is configured similar to that described in U.S. Pat. No. 7,082,325 and/or in U.S. Pat. No. 6,813,515, each of which are assigned to the common assignee of the present application and each of which is hereby fully incorporated by reference. It should be understood that the probe may have other configurations and other sets of components.

The clean margin status targets are defined 1904. To this end, the clean margin status targets may be selected from, but is not limited to: no abnormal tissue at the characterized tissue surface; no abnormal tissue up to a given depth from the characterized tissue surface, such as a 1 mm or 2 mm depth, or up to 20 mm depth. The probe is delivered to a tissue (step 1910), such as the tissue 1805 shown in FIGS. 18A-18C. The clean margin process achievement begins 1920, and the process enters a control cycle (dotted rectangle 1925). A first segment is characterized 1930, for example at a 'near zone' tissue surface (e.g. 0-20 mm), to determine, preferably in real-time, based upon the characterization of the tissue at the present segment, whether the first segment is characterized as having a clean margin 1940. The first segment may be for example one of the tissue segments 1831' or 1832'. A characterization result/data or a margin status of each examined segment may be recorded in a memory utility located for example in the probe, and may be further displayed on the computer screen. The margin status of each examined segment may be further transmitted to the external computer or to an external memory device such as a removable memory e.g. a DiskonKey or other small and portable memory device. The margin status of each segment which was recorded or saved may be used for example for additional procedures such as pathology procedure related to the examined tissue e.g. tissue 1805 or to a different body lumen or anatomical feature of a patient.

According to some embodiments of the present invention, a session data may be saved for example in a computerized system, such as the above described computerized system 95, for further analysis. The session data may include for example, a reconstructed three-dimensional image of a tissue portion (e.g. an examined tissue surface such as the tissue portion 1850), the coordinates and margin status of all segments in the tissue portion. The session data may be exported and transmitted to an external device/computer or to an external memory device such as a removable memory e.g. a DiskonKey or other small and portable memory device. The session data which was recorded or saved may be used, for example, in additional procedures, such as pathology procedures, related to the examined tissue, additional surgical or diagnostic procedures, related to the respective patient.

A segment margin status result may be defined as a positive result or negative result. If positive, e.g. the first segment is characterized as having a clean margin, then the probe is displaced and relocated to the next tissue segment to determine whether all segments of the tissue surface were characterized as having a clean margin (steps 1945, 1980, 1940). The relocation of the probe may be manual, semi-manual or automatic employing for example, a two-dimensional or three-dimensional computer controlled stage, as is known in the art. There may be a computer program which controls the stage and defines the sequence of moving the probe from one location or segment to the next. In cases, where the relocation is manual or semi-manual, the system may provide an operator with specific instructions on how and to whereto move the probe. If all the tissue segments are characterized as having a clean margin, then the achieving clean margin process is completed. If no, the probe is displaced and relocated to the next tissue segment to characterize the next tissue segment (step 1980) and determine whether the next tissue segment has a clean margin or not (step 1940). The next segment may be located, for example adjacent to or in proximity to the previously characterized segment. If the first characterized segment has no clean margin, then a tissue segment adjacent to the first tissue segment is removed 1950 from the body. The tissue removal may be done using an incision instrument, which may for example be attached to the probe to enable cutting and removing the tissue region while characterizing the respective tissue segment. The removed tissue segment or the surface of the tissue from where the tissue was removed is characterized 1960 for determining whether it has a clean margin. If negative, e.g. the removed tissue segment or the surface of the tissue from where the tissue was removed includes a clean margin, then the clean margin assessment process is continued and the process returns to step 1980 for characterizing the next segment. If positive, e.g. the removed tissue segment or the surface of the tissue from where the tissue segment was removed does not include a clean margin, then the process returns to step 1950 and the tissue adjacent to at least the location of the tissue segment at which there was no clean margin is removed from the body.

According to some embodiments of the present invention the output data relating to the margin status of for example all characterized tissue segments may be recorded and transmitted to the computer system and may be displayed on the computer screen. According to some embodiments of the present invention the clean margin process may be performed for providing a clean margin during a procedure for characterizing an anatomical feature. An example of anatomical feature may be a prostate.

FIG. 19B shows flowchart 2000 according to another example of the present invention. A probe or tool for characterizing a tissue is provided (step 2002), the probe/tool may include one or more tissue-type sensors, such as the above described tissue-type sensor 33, for determining the characteristics of a tissue surface, such as tissue surfaces 1831 or 1832, for example in the near zone volume of the tissue surface. The probe may be configured as the above described integrated tool 10 for clean-margin assessment, or may have other configurations and other sets of components.

The clean margin process targets are defined (step 2004). The clean margin process targets may be selected, as for example but is not limited to: no abnormal tissue at the characterized tissue surface; no abnormal tissue up to a given depth from the characterized tissue surface, such as a 1 mm or 2 mm depth, or up to 20 mm depth. The probe is delivered to a tissue (step 2010), such as the tissue 1805, or tissue portion 1850, shown in FIGS. 18a-18c. The clean margin process begins (step 2020). All the segments (1831' and or 1832') of the tissue surface 1831 and or 1832 are characterized (step 2030). The margin status of all segments is reordered (step 2040) or registered for example by a computerized apparatus, such as the apparatus 100 for clean-margin assessment, described hereinabove in conjunction with FIG. 1. The margin status which is based on the defined clean margin targets may be negative, e.g. the segment is characterized as having a clean margin, or positive, e.g. the segment is characterized as not having a clean margin.

According to some embodiments of the present invention the margin status of all segments which was reordered or registered may be used for determining an incision path, for example for decision-making during an operation as to the delimitation of the abnormal tissue e.g. the segments which were characterized as not having a clean margin.

The achieving clean margin process enters a control cycle (steps 2025) which includes the following: Based upon the margin status of each segment, it is determined, preferably in real time, whether all the tissue segments are characterized as having a clean margin (step 2050). If yes, e.g. all the tissue segments are characterized as having a clean margin then the achieving of a clean margin process is completed. If no, then tissue segments which correspond and/or are adjacent to the location of the tissue segments at which there was no clean margin are removed (step 2055), for example using a scalpel, or a diathermal knife. The removed tissue segments and/or the surface of the tissue from where the tissue was removed are characterized (step 2060), and their margin status is recorded (step 2070). Then, the clean margin process returns to the first step 2050 of the control cycle for determining whether the removed tissue and/or the surface of the tissue from where the tissue segments were removed are characterized as clean margin. The clean margin process is continued in the control cycle until the margin status of all the characterized tissue segments is clean.

Figure 20:
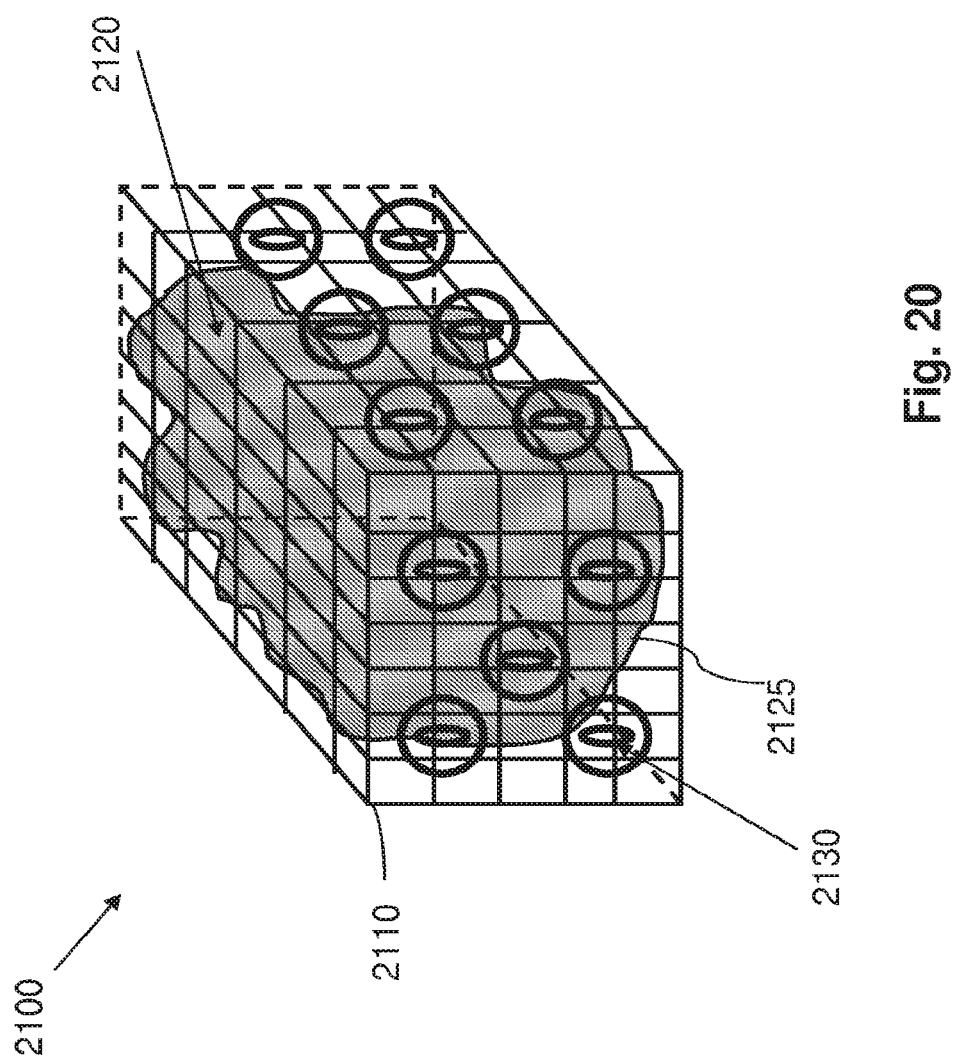
FIG. 20 exemplifies a device of the present invention for holding and characterizing a tissue or an anatomical feature during a clean-margin assessment process.

Reference is now made to FIG. 20 illustrating a device 2100 for holding and characterizing a tissue or an anatomical feature, for example during a clean-margin assessment process, in accordance with some embodiments of the present invention. The device 2100 includes a body or housing 2110, configured for receiving and holding a tissue or the tissue portion (e.g. as shown in FIGS. 18A-18C), or a body lumen portion, a skin portion or an anatomical feature. According to one embodiment of the present invention, one or more sensors such as tissue-type sensors 2130, or an array of sensors such as a rectangular array or matrix of optical sensor elements, may be attached or mounted on the housing 2110 for sensing and characterizing the tissue surface 2125, for example of an anatomical structure 2120, to indicate a clean margin.

The housing 2110 may be shaped to conform to the surface of the anatomical feature 2120. Therefore, the anatomical feature 2120 may be sensed or scanned from any direction, without being limited by the shape of the housing 2110. According to one embodiment of the present invention, the sensors or the array of sensors may be attached to the inner side of the housing 2110 for sensing or scanning for example an anatomical structure which is enclosed by the housing. According to another embodiment of the present invention, the sensors or the array of sensors may be attached to the outer side or surface of the housing 2110 for sensing or scanning for example an anatomical structure which surrounds the outer side of housing 2110. According to some embodiments of the present invention, one or more sensors such as the as tissue-type sensors 2130 may be attached to and cover the whole surface of the housing 2110, thus enabling sensing or scanning the whole surface of the anatomical structure simultaneity in real time.

The housing 2110 may be formed as a rigid body such as cube, or a sphere, or an ellipsoid. Additionally, or alternatively, the housing 2110 may be formed, for example as a flexible body such as a stretchable body, an expansible body, a sac-like mesh, a stretchable stocking, or a resilient cage.

Such housing 2110 may be similar to various embodiments described, for example, in international publication number WO 2006/092797, entitled "Device And Method For Transporting And Handling Tissue", assigned to the common assignee of the present application and incorporated herein by reference.

According to some embodiments of the present invention, a tissue surface, such as the tissue surface 2125, may be scanned or sensed by using a relative displacement between the housing and/or the sensors, e.g. by rotating the sensors 2130 or an array of sensors and/or the housing 2110, using for example a robotic arm or a motor. For example, one or more sensors 2130 may be connected to a robotic arm which is configured to move and rotate the sensors 2130 and scan the tissue surface 2125 of the anatomical feature 2120 to indicate the margin status at the anatomical feature 2125, while the housing 2110 holds the anatomical feature 2120. According to some other embodiments of the present invention, the housing 2110 may be rotated as it holds the anatomical feature 2120 and the sensors 2130 or the array of sensors may sense and/or scan the anatomical feature 2120 to indicate the margin status at the anatomical feature 2125, while the sensors or the array of sensors are stable and fixed.

The tissue surface 2125 may include a specific positional reference with respect to the body from which it was taken, or is being taken, and the device 2100 is designed to maintain the tissue positional reference, by providing, for example a rigid frame of reference for it.

The feature/tissue characterizing device 2100 may be applied to the feature/tissue after the tissue 2125 or the anatomical feature 2120 have been removed from the body, or while the tissue 2125 or the anatomical feature are being removed.

In operation, a tissue (such as the tissue 1805 or the tissue portion 1850 shown in FIGS. 18a-18c), a body lumen portion, a skin portion or an anatomical feature, such as the anatomical feature 2120 may be inserted into the device 2100, or may be attached to the outer surface of the housing 2110 for identifying whether there is a clean margin, for example at the tissue surface of the anatomical feature. The tissue or the anatomical feature 2120 is characterized, preferably in real time, by rotating the housing 2110 and/or the sensors 2130 of the device 2100 or by activating the array of sensors. Signals from the sensors 2130 are transferred for analysis to a computerized system, such as the computerized system 95 for clean-margin assessment, described hereinabove in conjunction with FIG. 1. If the anatomical feature 2120 is characterized as having a clean margin then the clean margin process is completed. If the anatomical feature does not have a clean margin then an additional anatomical feature adjacent to the anatomical feature which did not have a clean margin, or a tissue corresponding/adjacent to at least the location of the tissue at which there was no clean margin, is removed from the body as described hereinabove in conjunction with FIGS. 19a and 19b.

According to some embodiments of the present invention, the device 2100 may be constructed as a continuous surface carrying sensors, such as sensors 2130, mounted on its inner side. Such a continuous surface has an opening for connection to a vacuum source. The device 2100 may further include a mechanism for generating suction within it, for example by connecting it to a vacuum source. When suction (e.g. vacuum) is applied to the housing 2110 of device 2100, for example when a tissue portion is enclosed within the housing 2100, negative pressure present within the housing 2110 will result in the deformation of the housing so that its shape will match to the tissue within it, thereby attaching the tissue or the anatomical feature 2120 to the sensors 2130 or to the active areas thereof. Once the tissue within the housing has been attached to the sensor array active areas, a tissue characterization process is initiated.

Figure 21B:
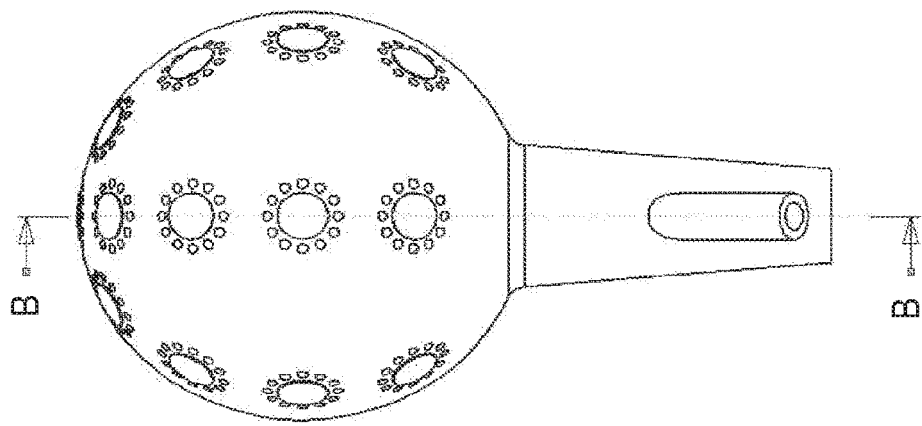
FIGS. 21A and 21B illustrate a side view and a three dimension view, respectively, of a sensor array frame structure.
Figure 21A:
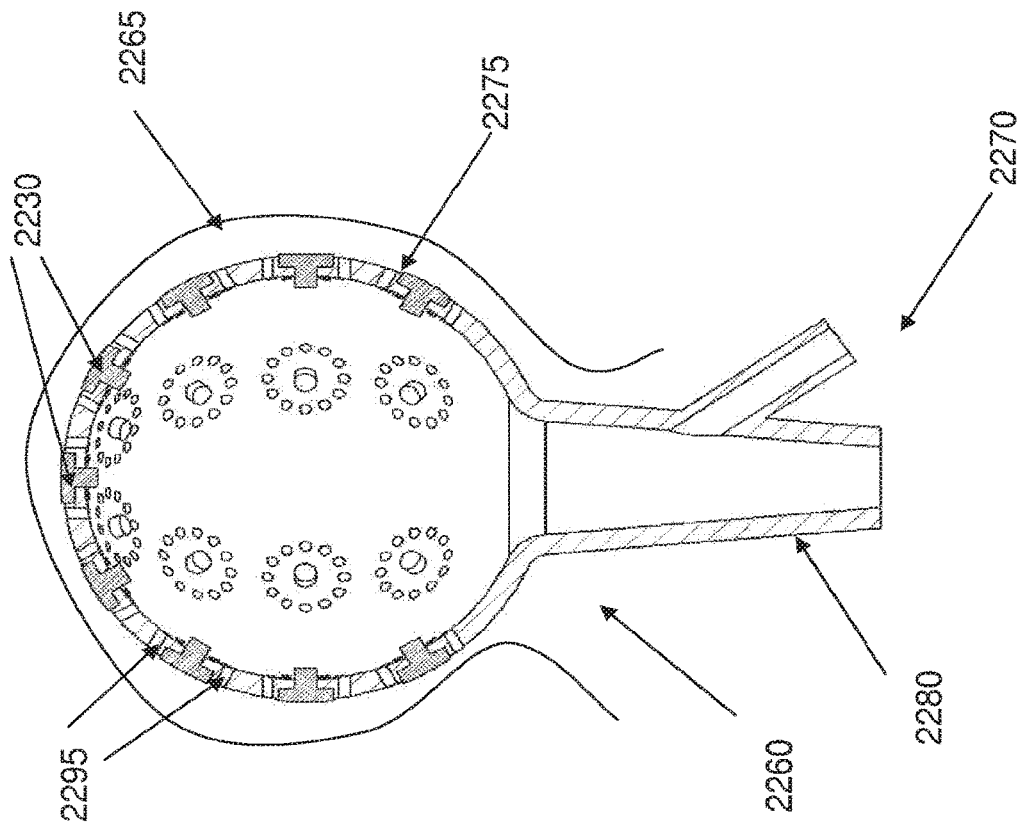

According to some embodiments of the present invention, as shown in FIG. 20 and more specifically in FIGS. 21A and 21B, one or more sensors such as array sensors 2230, may be mounted on or attached to the outer surface of a sensor array frame structure 2260 or the device 2100 to characterize tissue, such as tissue 2265 enclosing and/or surrounding the sensor array frame structure 2260 or device 2100. The sensor array frame structure 2260 or device 2100 may be formed, for example, but not limited to, as a sphere, an ellipsoid, a tube, or a shape conforming to a body anatomical feature. The sensor array structure 2260 further includes a signal communication bundle 2270 for transmitting and receiving signals from and to sensors 2230. The signal communication with the sensors 2230 may be performed, for example as described in co-pending, US application entitled "PROBES, SYSTEMS, AND METHODS FOR EXAMINING TISSUE ACCORDING TO THE DIELECTRIC PROPERTIES THEREOF" filed on May 1, 2007 and published as US 2008/0021343 whose disclosure is incorporated herein by reference Each of the sensors may have a dedicated signal communication line. Alternatively, a common signal communication line is employed associated with multiple sensors and operable with multiplexing, for example, time multiplexing, or wavelength multiplexing.

The tissue 2265 surrounding the sensor array structure may be in a form of a closed continuous tissue surface, for example a cavity or a closed lumen. The cavity may be either a natural body cavity, or a cavity formed by removal of tissue during a surgical procedure, for example partial mastectomy or lumpectomy breast cancer removal surgical procedures. The closed lumen may be, for example, a blocked or truncated or an artificially closed lumen.

According to some embodiments of the present invention, the sensor array structure 2260 may include a mechanism for generating suction within it, configured to enable a contact and release between the sensor array frame structure 2260 and the tissue 2265, ensuring a reliable and effective tissue-characterization.

As shown in the present example, the sensor array frame structure 2260 includes one or more connection locations (openings and possible appropriate connectors extending from said openings) 2280 for connecting a vacuum source (not shown) to the sensor array frame structure 2260, and one or more perforations (holes) 2295, arranged in a spaced-apart relationship within the surface of the structure 2260 to enable vacuum communication between the vacuum source and the outer surface 2275 of the structure 2260. When the sensor array structure 2260 is surrounded by a closed continuous tissue surface, such as tissue 2265, the holes 2295 enable vacuum communication between the vacuum source and the closed continuous tissue surface surrounding the sensor array structure.

In operation, for example during surgery, the sensor array frame structure 2260 is inserted, for example, into an opening in a closed continuous tissue surface. Following the insertion of the sensor array frame structure 2260, the opening of the closed continuous tissue surface is tightly attached around the connection location 2280, thus forming a closed continuous tissue surface with its only opening 2280 directly connected to the vacuum source. When vacuum (i.e. suction) from the vacuum source is applied to the interior of the sensor array structure, vacuum communication between the inner and outer surfaces of the sensor array structure and the closed continuous tissue surface is formed, due to the existence of holes 2295 across the structure surface. The negative pressure present at the outer surface of the sensor array structure 2260 results in the collapse of the closed continuous tissue surface 2265 and attachment of this surface onto the external surface of the sensor array structure 2260, where the sensors 2250 are located. Once the closed continuous tissue surface has attached itself to the sensor array active areas, a tissue characterization process is initiated.

It is expected that during the life of this patent many substrate measurement techniques and medical imaging methods will be developed and the scope of the invention is intended to include all such new substrate measurement techniques and medical imaging methods a priori.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Specifically, components and/or actions ascribed to exemplary embodiments of the invention and depicted as a single unit may be divided into subunits. Conversely, components and/or actions ascribed to exemplary embodiments of the invention and depicted as sub-units/individual actions may be combined into a single unit/action with the described/depicted function.

Alternatively, or additionally, features used to describe a method can be used to characterize an apparatus or system and features used to describe an apparatus or system can be used to characterize a method.

It should be further understood that the individual features described hereinabove can be combined in all possible combinations and sub-combinations to produce additional embodiments of the invention. The examples given above are only for purposes of illustration and are not intended to limit the scope of the invention which is defined solely by the following claims. Specifically, the invention has been described in the context of assaying an excised tissue mass and/or cavity resulting from excision but might also be used in non-medical applications including, but not limited to quarrying and/or mining. For example, a sequence of events described and/or claimed in the context of a method may be performed in any order.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The terms "include" and "have" and their conjugates as used herein mean "including but not necessarily limited to".

While this invention has been particularly shown and described with references to preferred embodiments thereof, it will be understood by those skilled in the art that various changes in form and details may be made therein without departing from the scope of the invention encompassed by the appended claims.

What is claimed is:

1. A substrate analysis system, the system comprising:
   a substrate position indicator fixedly positioned at a point on a surface of or inside a substrate;

a hand probe configured and operable to characterize the substrate at one or more individual points selected by a user on the surface of the substrate, the probe comprising:
- a data acquisition module configured and operable to engage the substrate surface at said one or more individual points and measure and/or characterize one or more parameters indicative of one or more dielectric properties of the substrate at the one or more individual points, and outputting corresponding one or more datum indicative of substrate status at the respective one or more individual points on the substrate surface, and
- a position determination module adapted to provide, concurrently with the one or more substrate status indicative datum, a position of the probe at each individual point of the one or more individual points;

a measurement module configured and operable to receive signals from at least one of the substrate position indicator and the position determination module of the probe and determine a relative position of said substrate position indicator and said probe at each of the one or more individual points; and a controller configured and operable to coordinate operation of said probe and said measurement module so that said relative position is determined for said each individual point of said one or more individual points;

wherein the system thereby determines for said each individual point of the one or more individual points engaged by the probe on the surface of the substrate: the location of the individual point on the substrate surface and the corresponding substrate status at the individual point on the surface of the substrate.

2. The substrate analysis system according to claim 1, wherein said measurement module comprises at least one position sensor configured and operable to determine a first position of the probe and a second position of the substrate position indicator; thereby enabling said measurement module to determine said relative position by comparing said first and second positions.

3. The substrate analysis system according to claim 1, wherein said substrate position indicator comprises a passive marker.

4. The substrate analysis system according to claim 1, wherein said substrate position indicator comprises an active marker.

5. The substrate analysis system according to claim 1, further comprising an imaging module configured and operable to produce image data depicting said probe and said substrate position indicator; wherein said measurement module determines said relative position from said image data.

6. The substrate analysis system according to claim 1, further comprising a registration module adapted to register said one or more status indicative datum and the corresponding locations on the substrate surface with medical image data.

7. The substrate analysis system according to claim 1, further comprising a registration module adapted to register local summaries of said one or more status indicative datum with medical image data.

8. The substrate analysis system according to claim 1, further comprising a procedure planning module configured and operable to calculate one or more paths serving in one or more treatment procedures at the substrate.

9. The substrate analysis system according to claim 8, wherein said treatment procedure comprises one or more of the following: cutting tissue, ablating tissue, implanting devices and injection of medicine.

10. The substrate analysis system according to claim 8, wherein said procedure planning module is configured and operable to accept user input pertaining to a planned path.

11. A surgical supervision system, the system comprising:
- the substrate analysis system according to claim 8;
- an input module configured and operable to receive a proposed path from said procedure planning module; and
- a guidance system configured and operable to output guidance instructions to guide a surgical tool in accordance with said proposed path.

12. The substrate analysis system as defined in claim 1, wherein said probe further comprises:
- a user input device; and
- a signal conduit adapted to relay electrical or optical signals to or from the substrate.

13. The substrate analysis system according to claim 12, wherein said user input device is configured to group said one or more substrate status indicative datum into one or more groups of data.

14. The substrate analysis system according to claim 12, wherein said probe further comprises:
- a lumen adapted to relay a negative pressure from an external vacuum source to said data acquisition module.

15. The substrate analysis system according to claim 14, wherein said probe further comprises:
- a user perceptible indicator configured and operable to indicate said substrate status.

16. The substrate analysis system according to claim 15, wherein said probe further comprises:
- a cutting tool mounted thereon.

17. The substrate analysis system according to claim 1, wherein said position determination module provides position coordinates defined relative to said substrate.

* * * * *